(12) United States Patent
Srivastava et al.

(10) Patent No.: US 11,883,655 B2
(45) Date of Patent: Jan. 30, 2024

(54) SYSTEMS AND METHODS FOR TREATMENT OF PANCREATIC CANCER

(71) Applicant: Boston Scientific Scimed, Inc., Maple Grove, MN (US)

(72) Inventors: Kyle Harish Srivastava, St. Paul, MN (US); Vijay Koya, Blaine, MN (US); Thomas Lee Williams, Blaine, MN (US); Miles Kealy, Minneapolis, MN (US); Nicholas Barron, Columbia Heights, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 17/182,436

(22) Filed: Feb. 23, 2021

(65) Prior Publication Data

US 2021/0260370 A1 Aug. 26, 2021

Related U.S. Application Data

(60) Provisional application No. 62/980,811, filed on Feb. 24, 2020.

(51) Int. Cl.
*A61N 1/36* (2006.01)
*A61N 1/40* (2006.01)
(Continued)

(52) U.S. Cl.
CPC ....... *A61N 1/36002* (2017.08); *A61N 1/0509* (2013.01); *A61N 1/08* (2013.01); *A61N 1/36007* (2013.01); *A61N 1/40* (2013.01)

(58) Field of Classification Search
CPC .... A61N 1/0509; A61N 1/08; A61N 1/36002; A61N 1/36007; A61N 1/36034;
(Continued)

(56) References Cited

U.S. PATENT DOCUMENTS

| | | |
|---|---|---|
| 4,016,886 A | 4/1977 | Doss et al. |
| 5,099,838 A | 3/1992 | Bardy |

(Continued)

FOREIGN PATENT DOCUMENTS

| | | |
|---|---|---|
| AU | 2005301103 | 5/2006 |
| AU | 2018354157 | 1/2021 |

(Continued)

OTHER PUBLICATIONS

"Optune®—Elevate Expectations / Patient Information and Operation Manual," Novocure™, www.optune.com, 46, pages, Jan. 2019., 46.

(Continued)

*Primary Examiner* — Carl H Layno
*Assistant Examiner* — Jane C Kalinock
(74) *Attorney, Agent, or Firm* — Pauly, DeVries Smith & Deffner LLC

(57) ABSTRACT

Embodiments herein relate to medical devices and methods for using the same to treat cancerous tumors within a bodily tissue. A medical device system herein can include an electric field generating circuit configured to generate one or more electric fields, and control circuitry. The system can include one or more electrodes disposed on a first stimulation lead to deliver the electric fields to a site of a cancerous tumor within a patient and one or more electrodes disposed on a second stimulation lead to deliver the electric fields to the site of a cancerous tumor within a patient. The first and second stimulation leads can be configured to be implanted on or about a duodenum. The electric field generating circuit can generate electric fields at frequencies selected from a range of between 10 kHz to 1 MHz. Other embodiments are also included herein.

20 Claims, 16 Drawing Sheets

(51) Int. Cl.
*A61N 1/05* (2006.01)
*A61N 1/08* (2006.01)

(58) Field of Classification Search
CPC .. A61N 1/36017; A61N 1/40; A61N 1/37518;
A61B 5/6879; A61B 5/6882; A61B
5/6883; A61B 5/6884; A61B 17/0401;
A61B 5/076; A61B 2017/0435; A61B
2017/0445
USPC .......................................................... 607/40
See application file for complete search history.

(56) References Cited

U.S. PATENT DOCUMENTS

| | | | |
|---|---|---|---|
| 5,324,328 | A | 6/1994 | Li et al. |
| 5,397,342 | A | 3/1995 | Heil et al. |
| 5,458,597 | A | 10/1995 | Edwards et al. |
| 5,582,609 | A | 12/1996 | Swanson et al. |
| 5,834,051 | A | 11/1998 | Woloszko et al. |
| 6,366,808 | B1 | 4/2002 | Schroeppel et al. |
| 6,673,623 | B1 | 1/2004 | Huberman |
| 6,868,289 | B2 | 3/2005 | Palti |
| 6,920,361 | B2 | 7/2005 | Williams |
| 7,162,310 | B2 | 1/2007 | Doan |
| 7,449,021 | B2 | 11/2008 | Underwood et al. |
| 7,524,274 | B2 | 4/2009 | Patrick et al. |
| 7,565,205 | B2 | 7/2009 | Palti |
| 7,656,205 | B2 | 2/2010 | Chen et al. |
| 7,715,921 | B2 | 5/2010 | Palti |
| 7,720,549 | B2 | 5/2010 | Schroeppel et al. |
| 7,805,201 | B2 | 9/2010 | Palti |
| 7,809,441 | B2 | 10/2010 | Kane et al. |
| 7,890,183 | B2 | 2/2011 | Palti et al. |
| 7,917,227 | B2 | 3/2011 | Palti |
| 8,002,821 | B2 | 8/2011 | Stinson |
| 8,019,414 | B2 | 9/2011 | Palti |
| 8,170,648 | B2 | 5/2012 | Field et al. |
| 8,175,698 | B2 | 5/2012 | Palti et al. |
| 8,229,555 | B2 | 7/2012 | Palti |
| RE43,618 | E | 8/2012 | Palti |
| 8,244,345 | B2 | 8/2012 | Palti |
| 8,406,870 | B2 | 3/2013 | Palti |
| 8,447,395 | B2 | 5/2013 | Palti et al. |
| 8,447,396 | B2 | 5/2013 | Palti et al. |
| 8,465,533 | B2 | 6/2013 | Palti |
| 8,483,821 | B2 | 7/2013 | Averina et al. |
| 8,500,713 | B2 | 8/2013 | Ferek-Petric |
| 8,706,261 | B2 | 4/2014 | Palti |
| 8,715,203 | B2 | 5/2014 | Palti |
| 8,718,756 | B2 | 5/2014 | Palti |
| 8,764,675 | B2 | 7/2014 | Palti |
| 8,805,466 | B2 | 8/2014 | Salahieh et al. |
| 8,956,352 | B2 | 2/2015 | Mauch et al. |
| 9,005,100 | B2 | 4/2015 | Gnanashanmugam et al. |
| 9,023,090 | B2 | 5/2015 | Palti |
| 9,023,091 | B2 | 5/2015 | Palti |
| 9,039,674 | B2 | 5/2015 | Palti et al. |
| 9,056,203 | B2 | 6/2015 | Palti et al. |
| 9,179,974 | B2 | 11/2015 | Ku et al. |
| 9,248,278 | B2 | 2/2016 | Crosby et al. |
| 9,283,383 | B2 | 3/2016 | Osypka |
| 9,308,039 | B2 | 4/2016 | Azure |
| 9,387,323 | B2 | 7/2016 | Fleischhacker et al. |
| 9,427,278 | B2 | 8/2016 | Swanson |
| 9,440,068 | B2 | 9/2016 | Palti et al. |
| 9,526,911 | B1 | 12/2016 | Azure et al. |
| 9,630,022 | B2 | 4/2017 | Bourke et al. |
| 9,655,669 | B2 | 5/2017 | Palti et al. |
| 9,750,934 | B2 | 9/2017 | Palti et al. |
| 9,833,617 | B2 | 12/2017 | Travers et al. |
| 9,910,453 | B2 | 3/2018 | Wasserman et al. |
| 10,029,117 | B2 | 7/2018 | Bourke |
| 10,238,862 | B2 | 3/2019 | Cook et al. |
| 10,265,530 | B1 | 4/2019 | Perryman et al. |
| 10,376,177 | B2 | 8/2019 | Valvano et al. |
| 10,471,254 | B2 | 11/2019 | Sano et al. |
| 11,191,956 | B2 | 12/2021 | Giladi et al. |
| 11,331,493 | B2 | 5/2022 | Pivonka et al. |
| 11,338,135 | B2 | 5/2022 | Schmidt et al. |
| 11,420,049 | B2 | 8/2022 | Schmidt et al. |
| 11,607,542 | B2 | 3/2023 | Schmidt et al. |
| 11,691,006 | B2 | 7/2023 | Schmidt et al. |
| 11,712,561 | B2 | 8/2023 | Schmidt et al. |
| 2001/0044643 | A1 | 11/2001 | Vitz |
| 2002/0026183 | A1 | 2/2002 | Simpson |
| 2002/0049485 | A1 | 4/2002 | Smits |
| 2002/0065544 | A1 | 5/2002 | Smits |
| 2003/0020416 | A1 | 1/2003 | Kobayashi |
| 2003/0069623 | A1* | 4/2003 | Stypulkowski ...... A61N 1/0551 607/117 |
| 2003/0204161 | A1 | 10/2003 | Ferek-Petric |
| 2004/0010290 | A1 | 1/2004 | Schroeppel et al. |
| 2004/0158288 | A1 | 8/2004 | Keisari et al. |
| 2004/0162600 | A1 | 8/2004 | Williams |
| 2004/0176804 | A1 | 9/2004 | Palti |
| 2004/0215296 | A1 | 10/2004 | Ganz et al. |
| 2005/0004507 | A1 | 1/2005 | Schroeppel et al. |
| 2005/0043894 | A1 | 2/2005 | Fernandez |
| 2005/0096584 | A1 | 5/2005 | Ferek-Petric |
| 2005/0209642 | A1 | 9/2005 | Palti |
| 2005/0222623 | A1 | 10/2005 | Kroll et al. |
| 2005/0222646 | A1 | 10/2005 | Kroll et al. |
| 2005/0240173 | A1 | 10/2005 | Palti |
| 2005/0288730 | A1 | 12/2005 | Deem et al. |
| 2006/0024802 | A1 | 2/2006 | Muller et al. |
| 2006/0149341 | A1 | 7/2006 | Palti |
| 2006/0190053 | A1 | 8/2006 | Dobak |
| 2006/0259099 | A1 | 11/2006 | Goetz et al. |
| 2006/0282122 | A1 | 12/2006 | Palti |
| 2007/0033660 | A1 | 2/2007 | Palti |
| 2007/0179550 | A1 | 8/2007 | Dennis et al. |
| 2007/0225766 | A1 | 9/2007 | Palti |
| 2007/0239213 | A1 | 10/2007 | Palti |
| 2007/0239244 | A1 | 10/2007 | Morgan et al. |
| 2007/0270675 | A1 | 11/2007 | Kane et al. |
| 2007/0270916 | A1 | 11/2007 | Fischell et al. |
| 2008/0058669 | A1 | 3/2008 | Kroll |
| 2008/0071350 | A1 | 3/2008 | Stinson et al. |
| 2008/0086073 | A1 | 4/2008 | McDaniel |
| 2008/0097424 | A1 | 4/2008 | Wizeman et al. |
| 2008/0195227 | A1 | 8/2008 | Boling et al. |
| 2008/0208271 | A1 | 8/2008 | Sih et al. |
| 2008/0275524 | A1 | 11/2008 | Furness et al. |
| 2009/0076500 | A1 | 3/2009 | Azure |
| 2009/0192381 | A1 | 7/2009 | Brockway et al. |
| 2009/0234211 | A1 | 9/2009 | Li et al. |
| 2010/0016936 | A1 | 1/2010 | Stevenson et al. |
| 2010/0198298 | A1 | 8/2010 | Schulman et al. |
| 2010/0261994 | A1 | 10/2010 | Davalos et al. |
| 2010/0298895 | A1 | 11/2010 | Ghaffari et al. |
| 2010/0331938 | A1 | 12/2010 | Sommer et al. |
| 2011/0071608 | A1 | 3/2011 | Fleischhacker et al. |
| 2011/0125215 | A1 | 5/2011 | Goetz et al. |
| 2011/0137229 | A1 | 6/2011 | Palti et al. |
| 2011/0238057 | A1 | 9/2011 | Moss et al. |
| 2012/0035616 | A1 | 2/2012 | Olsen et al. |
| 2012/0130444 | A1 | 5/2012 | Wei et al. |
| 2012/0158072 | A1 | 6/2012 | Venook et al. |
| 2012/0158122 | A1 | 6/2012 | Mattson et al. |
| 2012/0203307 | A1 | 8/2012 | Schroeppel et al. |
| 2012/0232615 | A1 | 9/2012 | Barolat et al. |
| 2012/0283726 | A1 | 11/2012 | Palti |
| 2013/0023946 | A1 | 1/2013 | Valvano et al. |
| 2013/0165916 | A1 | 6/2013 | Mathur et al. |
| 2013/0204068 | A1 | 8/2013 | Gnanashanmugam et al. |
| 2013/0261706 | A1 | 10/2013 | Mirro et al. |
| 2013/0261711 | A1 | 10/2013 | Sivo |
| 2013/0289649 | A1 | 10/2013 | Averina et al. |
| 2013/0289664 | A1 | 10/2013 | Johanek |
| 2013/0310898 | A1 | 11/2013 | Ollivier et al. |
| 2014/0005753 | A1 | 1/2014 | Carbunaru |
| 2014/0052227 | A1 | 2/2014 | Wahlstrand et al. |
| 2014/0107511 | A1 | 4/2014 | Banet et al. |
| 2014/0142670 | A1 | 5/2014 | Radhakrishnan et al. |

(56) References Cited

U.S. PATENT DOCUMENTS

| | | |
|---|---|---|
| 2014/0276781 A1 | 9/2014 | Beani et al. |
| 2014/0276811 A1 | 9/2014 | Koblish et al. |
| 2014/0350653 A1 | 11/2014 | Shiroff et al. |
| 2015/0005804 A1 | 1/2015 | Franano et al. |
| 2015/0066024 A1 | 3/2015 | Azure |
| 2015/0134022 A1 | 5/2015 | Lee et al. |
| 2015/0180161 A1 | 6/2015 | Olson et al. |
| 2015/0182282 A1 | 7/2015 | Zemel et al. |
| 2015/0320995 A1 | 11/2015 | Nazareth et al. |
| 2015/0374992 A1 | 12/2015 | Crosby et al. |
| 2016/0022986 A1 | 1/2016 | Travers et al. |
| 2016/0029960 A1 | 2/2016 | Toth et al. |
| 2016/0068598 A1 | 3/2016 | Yan et al. |
| 2016/0082258 A1 | 3/2016 | Kramer et al. |
| 2016/0128767 A1 | 5/2016 | Azamian et al. |
| 2016/0129276 A1 | 5/2016 | Fried et al. |
| 2016/0250476 A1 | 9/2016 | Kaemmerer et al. |
| 2016/0250483 A1 | 9/2016 | Klimovitch et al. |
| 2016/0331459 A1 | 11/2016 | Townley et al. |
| 2016/0346536 A1 | 12/2016 | Palti et al. |
| 2017/0007310 A1 | 1/2017 | Rajagopalan et al. |
| 2017/0035496 A1 | 2/2017 | Nagale et al. |
| 2017/0049514 A1 | 2/2017 | Cosman |
| 2017/0065339 A1 | 3/2017 | Mickelsen |
| 2017/0105793 A1 | 4/2017 | Cao et al. |
| 2017/0120041 A1 | 5/2017 | Wenger et al. |
| 2017/0173340 A1 | 6/2017 | Gupte et al. |
| 2017/0189098 A1 | 7/2017 | Azure et al. |
| 2017/0215939 A1 | 8/2017 | Palti et al. |
| 2017/0251976 A1 | 9/2017 | Schouenborg |
| 2017/0266371 A1 | 9/2017 | Leonhardt et al. |
| 2017/0281934 A1 | 10/2017 | Giladi et al. |
| 2017/0281955 A1 | 10/2017 | Maile et al. |
| 2017/0312501 A1 | 11/2017 | Bornzin et al. |
| 2017/0333702 A1* | 11/2017 | Barner ............... A61N 1/37518 |
| 2018/0001075 A1 | 1/2018 | Kirson et al. |
| 2018/0001078 A1 | 1/2018 | Kirson et al. |
| 2018/0008708 A1 | 1/2018 | Giladi et al. |
| 2018/0021563 A1 | 1/2018 | Van De Stolpe et al. |
| 2018/0050200 A1 | 2/2018 | Wasserman et al. |
| 2018/0110978 A1 | 4/2018 | Beebe et al. |
| 2018/0154142 A1 | 6/2018 | Guo et al. |
| 2018/0221088 A1 | 8/2018 | Govari et al. |
| 2018/0246079 A1 | 8/2018 | Wang et al. |
| 2018/0289954 A1 | 10/2018 | Hebb et al. |
| 2019/0008555 A1 | 1/2019 | O'Mahony |
| 2019/0117969 A1 | 4/2019 | Schmidt et al. |
| 2019/0117970 A1 | 4/2019 | Schmidt et al. |
| 2019/0117971 A1 | 4/2019 | Schmidt et al. |
| 2019/0117972 A1* | 4/2019 | Schmidt ............... A61B 18/18 |
| 2019/0117973 A1 | 4/2019 | Schmidt et al. |
| 2019/0255344 A1 | 8/2019 | Carter et al. |
| 2019/0321624 A1* | 10/2019 | De Kock ............... A61N 1/057 |
| 2020/0009377 A1 | 1/2020 | Chang et al. |
| 2020/0330756 A1 | 10/2020 | Schmidt et al. |
| 2020/0330757 A1 | 10/2020 | Schmidt et al. |
| 2020/0330758 A1 | 10/2020 | Schmidt et al. |
| 2020/0338344 A1 | 10/2020 | Schmidt et al. |
| 2020/0338345 A1 | 10/2020 | Schmidt et al. |
| 2020/0338346 A1 | 10/2020 | Schmidt et al. |
| 2021/0339015 A1* | 11/2021 | Dinsmoor ............... A61B 5/686 |
| 2022/0241586 A1* | 8/2022 | Spehr ................... A61M 25/04 |
| 2022/0288388 A1* | 9/2022 | Rondoni ............... A61N 1/3606 |
| 2022/0296907 A1 | 9/2022 | Schmidt et al. |
| 2023/0218894 A1 | 7/2023 | Arnholt et al. |

FOREIGN PATENT DOCUMENTS

| | | |
|---|---|---|
| AU | 2018354159 | 2/2021 |
| CN | 101693875 | 4/2010 |
| CN | 202365923 | 8/2012 |
| CN | 204698678 | 10/2015 |
| CN | 106823145 | 6/2017 |
| CN | 111263618 | 6/2020 |
| CN | 111263656 | 6/2020 |
| CN | 111278504 | 6/2020 |
| CN | 111432872 | 7/2020 |
| CN | 111465429 | 7/2020 |
| EP | 2161054 | 3/2010 |
| EP | 2281603 | 2/2011 |
| EP | 2942023 | 11/2015 |
| EP | 3700451 | 9/2020 |
| EP | 3700621 | 9/2020 |
| EP | 3700623 | 9/2020 |
| EP | 3700626 | 9/2020 |
| EP | 3700627 | 9/2020 |
| JP | 2006513739 | 4/2006 |
| JP | 2007533389 | 11/2007 |
| JP | 2008515544 | 5/2008 |
| JP | 2008532564 | 8/2008 |
| JP | 2008541974 | 11/2008 |
| JP | 2011030734 | 2/2011 |
| JP | 2017504404 | 2/2017 |
| JP | 2021500200 | 1/2021 |
| JP | 2021500201 | 1/2021 |
| JP | 2021500202 | 1/2021 |
| JP | 2021500203 | 1/2021 |
| JP | 2021500204 | 1/2021 |
| TW | 201039699 | 11/2010 |
| WO | 9513113 | 5/1995 |
| WO | 9526911 | 10/1995 |
| WO | 9639966 | 12/1996 |
| WO | 0158371 | 8/2001 |
| WO | 0167098 | 9/2001 |
| WO | 2005115535 | 12/2005 |
| WO | 2006041881 | 4/2006 |
| WO | 2006047833 | 5/2006 |
| WO | 2008089360 | 7/2008 |
| WO | 2009036457 | 3/2009 |
| WO | 2009036459 | 3/2009 |
| WO | 2013052590 | 4/2013 |
| WO | 2015100451 | 7/2015 |
| WO | 2016065263 | 4/2016 |
| WO | 2016149575 | 9/2016 |
| WO | 2016168485 | 10/2016 |
| WO | 2016179712 | 11/2016 |
| WO | 2016199142 | 12/2016 |
| WO | 2017123981 | 7/2017 |
| WO | 2018207103 | 11/2018 |
| WO | 2019084003 | 5/2019 |
| WO | 2019084011 | 5/2019 |
| WO | 2019084013 | 5/2019 |
| WO | 2019084016 | 5/2019 |
| WO | 2019084021 | 5/2019 |
| WO | 2020219336 | 10/2020 |
| WO | 2020219337 | 10/2020 |
| WO | 2020219339 | 10/2020 |
| WO | 2020219517 | 10/2020 |
| WO | 2020219519 | 10/2020 |
| WO | 2020219521 | 10/2020 |
| WO | 2023137008 | 7/2023 |

OTHER PUBLICATIONS

"Communication Pursuant to Article 94(3) EPC," for European Patent Application No. 18801137.3 dated Mar. 5, 2021 (4 pages).

"Communication Pursuant to Article 94(3) EPC," for European Patent Application No. 18801138.1 dated Jun. 7, 2021 (7 pages).

Di Sebastiano, Andrea R. et al., "Preclinical Outcomes of Intratumoral Modulation Therapy for Glioblastoma," Scientific Reports (2018) 8:7301 (11 pages).

"Examination Report," for Australian Patent Application No. 2018354162 dated Apr. 21, 2021 (5 pages).

"Examination Report," for Australian Patent Application No. 2018354162 dated Feb. 4, 2021 (5 pages).

File History for U.S. Appl. No. 16/166,957 downloaded Jun. 9, 2021 (592 pages).

File History for U.S. Appl. No. 16/167,079 downloaded Jun. 9, 2021 (413 pages).

File History for U.S. Appl. No. 16/167,087 downloaded Jun. 9, 2021 (412 pages).

File History for U.S. Appl. No. 16/167,116 downloaded Jun. 9, 2021 (369 pages).

(56) References Cited

OTHER PUBLICATIONS

File History for U.S. Appl. No. 16/167,140 downloaded Jun. 9, 2021 (275 pages).
"First Examination Report," for Australian Patent Application No. 2018354149 dated Jul. 29, 2020 (5 pages).
"First Examination Report," for Australian Patent Application No. 2018354157 dated Jul. 31, 2020 (5 pages).
"First Examination Report," for Australian Patent Application No. 2018354159 dated Aug. 12, 2020 (5 pages).
"First Examination Report," for Australian Patent Application No. 2018354162 dated Sep. 29, 2020 (8 pages).
"First Examination Report," for Australian Patent Application No. 2018354167 dated Sep. 14, 2020 (5 pages).
Giladi, Moshe et al., "Mitotic Spindle Disruption by Alternating Electric Fields Leads to Improper Chromosome Segregation and Mitotic Catastrophe in Cancer Cells," Sci Rep 5, 18046 (2016), 16 pages.
"International Preliminary Report on Patentability," for PCT Application No. PCT/US2018/057104 dated May 7, 2020 (8 pages).
"International Preliminary Report on Patentability," for PCT Application No. PCT/US2018/057115 dated May 7, 2020 (9 pages).
"International Preliminary Report on Patentability," for PCT Application No. PCT/US2018/057117 dated May 7, 2020 (8 pages).
"International Preliminary Report on Patentability," for PCT Application No. PCT/US2018/057120 dated May 7, 2020 (8 pages).
"International Preliminary Report on Patentability," for PCT Application No. PCT/US2018/057127 dated May 7, 2020 (8 pages).
"International Search Report and Written Opinion," for PCT Application No. PCT/US2018/057104 dated Dec. 20, 2018 (14 pages).
"International Search Report and Written Opinion," for PCT Application No. PCT/US2018/057115 dated Jan. 4, 2019 (13 pages).
"International Search Report and Written Opinion," for PCT Application No. PCT/US2018/057117 dated Dec. 20, 2018 (14 pages).
"International Search Report and Written Opinion," for PCT Application No. PCT/US2018/057120 dated Dec. 19, 2018 (14 pages).
"International Search Report and Written Opinion," for PCT Application No. PCT/US2018/057127 dated Jan. 18, 2019 (12 pages).
"International Search Report and Written Opinion," for PCT Application No. PCT/US2020/028508 dated Aug. 3, 2020 (13 pages).
"International Search Report and Written Opinion," for PCT Application No. PCT/US2020/028509 dated Jun. 30, 2020 (15 pages).
"International Search Report and Written Opinion," for PCT Application No. PCT/US2020/028512 dated Jul. 13, 2020 (14 pages).
"International Search Report and Written Opinion," for PCT Application No. PCT/US2020/029270 dated Oct. 26, 2020 (19 pages).
"International Search Report and Written Opinion," for PCT Application No. PCT/US2020/029274 dated Aug. 28, 2020 (19 pages).
"International Search Report and Written Opinion," for PCT Application No. PCT/US2020/029277 dated Jul. 13, 2020 (15 pages).
"Invitation to Pay Additional Fees," for PCT Application No. PCT/US2020/029270 dated Aug. 28, 2020 (14 pages).
"Invitation to Pay Additional Fees," for PCT Application No. PCT/US2020/029274 dated Jul. 7, 2020 (13 pages).
Kirson, Eilon D et al., "Disruption of Cancer Cell Replication by Alternating Electric Fields," Cancer Research 64, 3288-3295, May 1, 2004 (8 pages).
"Non-Final Office Action," for U.S. Appl. No. 16/855,421 dated May 28, 2021 (37 pages).
"Novocure Announces Launch of the inovitro™," Laboratory Research System, Press Release, 2 pages, Nov. 21, 2013., 2 pages.
"Office Action," for Canadian Patent Application No. 3,079,289 dated May 28, 2021 (4 pages).
"Office Action," for Japanese Patent Application No. 2020-542718 dated Feb. 9, 2021 11 pages) with English Translation.
"Office Action," for Japanese Patent Application No. 2020-542721 dated Feb. 9, 2021 (10 pages) with English Summary.
"Office Action," for Japanese Patent Application No. 2020-542722 dated Feb. 9, 2021 (5 pages) with English Summary.
"Response to Communication Pursuant to Rules 161 (1) and 162 EPC," for European Patent Application No. 18800411.3 filed Dec. 9, 2020 (11 pages).
"Response to Communication Pursuant to Rules 161 (1) and 162 EPC," for European Patent Application No. 18801134.0 filed Dec. 11, 2020 (9 pages).
"Response to Communication Pursuant to Rules 161(1) and 162 EPC," for European Patent Application No. 18801136.5 filed Dec. 10, 2020 (8 pages).
"Response to Communication Pursuant to Rules 161(1) and 162 EPC," for European Patent Application No. 18801137.3 filed Dec. 10, 2020 (7 pages).
"Response to Communication Pursuant to Rules 161 (1) and 162 EPC," for European Patent Application No. 18801138.1 filed Dec. 11, 2020 (16 pages).
"Response to Examination Report," for Australian Patent Application No. 2018354149 filed Dec. 21, 2020 (14 pages).
"Response to Examination Report," for Australian Patent Application No. 2018354157 filed Dec. 31, 2020 (17 pages).
"Response to Examination Report," for Australian Patent Application No. 2018354159 filed Jan. 18, 2021 (21 pages).
"Response to Examination Report," for Australian Patent Application No. 2018354162 filed Jan. 28, 2021 (15 pages).
"Response to Examination Report," for Australian Patent Application No. 2018354162 filed Mar. 30, 2021 (15 pages).
"Response to Examination Report," for Australian Patent Application No. 2018354167 filed Jan. 28, 2021 (17 pages).
"Response to Second Examination Report," for Australian Patent Application No. 2018354149 filed Apr. 13, 2021 (19 pages).
"Second Examination Report," for Australian Patent Application No. 2018354149 dated Jan. 8, 2021 (4 pages).
Wang, Lijun et al., "Tumour Cell Membrane Poration and Ablation by Pulsed Low-Intensity Electric Field with Carbon Nanotubes," Int. J. Mol. Sci. 2015, 16, 6890-6901 (12 pages).
Xu, Hu et al., "In Vitro Validation of Intratumoral Modulation Therapy for Glioblastoma," Anticancer Research 36:71-80 (2016), 10 pages.
"Communication Pursuant to Article 94(3) EPC," for European Patent Application No. 18801137.3 dated Sep. 15, 2021 (4 pages).
"Decision of Rejection," for Japanese Patent Application No. 2020-54219 dated Oct. 19, 2021 (6 pages) with English Translation.
"Final Office Action," for U.S. Appl. No. 16/167,140 dated Dec. 27, 2021 (30 pages).
"Final Office Action," for U.S. Appl. No. 16/850,720 dated Nov. 15, 2021 (15 pages).
"Final Office Action," for U.S. Appl. No. 16/855,421 dated Nov. 5, 2021 (25 pages).
"International Preliminary Report on Patentability," for PCT Application No. PCT/US2020/028508 dated Nov. 4, 2021 (8 pages).
"International Preliminary Report on Patentability," for PCT Application No. PCT/US2020/028509 dated Nov. 4, 2021 (9 pages).
"International Preliminary Report on Patentability," for PCT Application No. PCT/US2020/028512 dated Nov. 4, 2021 (8 pages).
"International Preliminary Report on Patentability," for PCT Application No. PCT/US2020/029270 dated Nov. 4, 2021 (11 pages).
"International Preliminary Report on Patentability," for PCT Application No. PCT/US2020/029274 dated Nov. 4, 2021 (13 pages).
"International Preliminary Report on Patentability," for PCT Application No. PCT/US2020/029277 dated Nov. 4, 2021 (10 pages).
"Non-Final Office Action," for U.S. Appl. No. 16/166,957 dated Dec. 22, 2021 (39 pages).
"Non-Final Office Action," for U.S. Appl. No. 16/167,087 dated Dec. 22, 2021 (24 pages).
"Office Action," for Canadian Patent Application No. 3,079,316 dated Oct. 27, 2021 (4 pages).
"Office Action," for Japanese Patent Application No. 2020-542718 dated Oct. 19, 2021 (3 pages) No English Translation.
"Office Action," for Japanese Patent Application No. 2020-542721 dated Jan. 4, 2022 (2 pages) No English Translation.
"Office Action," for Japanese Patent Application No. 2020-542722 dated Oct. 26, 2021 (9 pages) with English Translation.

(56) References Cited

OTHER PUBLICATIONS

"Response to Communication Pursuant to Article 94(3) EPC," for European Patent Application No. 18801138.1 filed Oct. 15, 2021 (10 pages).
"Response to Examination Report," for Canadian Patent Application No. 3,079,213 filed Nov. 10, 2021 (13 pages).
"Response to Examination Report," for Canadian Patent Application No. 3,079,282 filed Nov. 10, 2021 (13 pages).
"Response to Final Rejection mailed on," dated Aug. 2, 2021 for U.S. Appl. No. 16/167,087, submitted via EFS-Web on Nov. 1, 2021, 12 pages.
"Response to Final Rejection," dated Jun. 23, 2021 and the Advisory Action dated Oct. 15, 2021 for U.S. Appl. No. 16/167,079, submitted via EFS-Web on Oct. 21, 2021, 19 pages.
"Response to Final Rejection," dated Nov. 5, 2021 for U.S. Appl. No. 16/855,421, submitted via EFS-Web on Jan. 5, 2022, 11 pages.
"Response to Non-Final Rejection," dated Aug. 24, 2021 for U.S. Appl. No. 16/850,720, submitted via EFS-Web on Nov. 1, 2021, 11 pages.
"Response to Non-Final Rejection," dated Sep. 3, 2021 for U.S. Appl. No. 16/167,116, submitted via EFS-Web on Nov. 2, 2021, 14 pages.
"Response to Non-Final Rejection," dated Sep. 8, 2021 for U.S. Appl. No. 16/855,433, submitted via EFS-Web on Nov. 2, 2021, 12 pages.
"Response to Office Action," for Canadian Patent Application No. 3,079,314 filed Nov. 12, 2021 (14 pages).
"Response to Office Action," for Canadian Patent Application No. 3,079,316 filed Dec. 31, 2021 (15 pages).
"Second Office Action," for Chinese Patent Application No. 201880068896.3 dated Oct. 20, 2021 (6 pages), No. English translation.
"Communication Pursuant to Article 94(2) EPC," for European Patent Application No. 18801138.1 dated Jun. 7, 2021 (7 pages).
"Examination Report," for Canadian Patent Application No. 3,079,213 dated Jul. 12, 2021 (4 pages).
"Examination Report," for Canadian Patent Application No. 3,079,282 dated Jul. 14, 2021 (4 pages).
"Examination Report," for Canadian Patent Application No. 3,079,314 dated Jul. 14, 2021 (4 pages).
"Final Office Action," for U.S. Appl. No. 16/167,079 dated Jun. 23, 2021 (34 pages).
"Final Office Action," for U.S. Appl. No. 16/167,087 dated Aug. 2, 2021 (25 pages).
"First Office Action," for Chinese Patent Application No. 201880068896.3 dated Apr. 13, 2021 (17 pages) with English Summary.
"International Search Report and Written Opinion," for PCT Application No. PCT/US2021/019160 dated Jun. 2, 2021 (15 pages).
"Non-Final Office Action," for U.S. Appl. No. 16/167,087 dated Mar. 31, 2021 (28 pages).
"Non-Final Office Action," for U.S. Appl. No. 16/167,140 dated Jul. 12, 2021 (32 pages).
"Office Action," for Japanese Patent Application No. 2020-542719 dated Jun. 1, 2021 (9 pages) with English Translation.
"Office Action," for Japanese Patent Application No. 2020-542720 dated May 11, 2021 (13 pages) with English Translation.
"Response to Examination Report," for Australian Patent Application No. 2018354162 filed Jul. 13, 2021 (18 pages).
"Response to Final Rejection," dated May 14, 2021 for U.S. Appl. No. 16/166,957, submitted via EFS-Web on Aug. 5, 2021, 18 pages.
"Response to Non-Final Rejection," dated Jan. 6, 2021 for U.S. Appl. No. 16/267,079, submitted via EFS-Web on Apr. 6, 2021, 19 pages.
"Response to Non-Final Rejection," dated Mar. 31, 2021 for U.S. Appl. No. 16/167,087, submitted via EFS-Web on Jun. 23, 2021, 12 pages.
"Response to Non-Final Rejection," dated May 28, 2021 for U.S. Appl. No. 16/855,421, submitted via EFS-Web on Aug. 20, 2021, 11 pages.
"First Office Action," for Chinese Patent Application No. 201880078117.8 dated Jul. 20, 2021 (14 pages) with English Summary.
"Non-Final Office Action," for U.S. Appl. No. 16/167,116 dated Sep. 3, 2021 (29 pages).
"Non-Final Office Action," for U.S. Appl. No. 16/850,720 dated Aug. 24, 2021 (32 pages).
"Non-Final Office Action," for U.S. Appl. No. 16/855,433 dated Sep. 8, 2021 (32 pages).
"Response to Final Rejection," dated Jun. 23, 2021 for U.S. Appl. No. 16/167,079, submitted via EFS-Web on Sep. 9, 2021, 16 pages.
"Response to Final Rejection," dated May 14, 2021 and Advisory Action dated Aug. 26, 2021 for U.S. Appl. No. 16/166,957, submitted via EFS-Web on Sep. 10, 2021.
"Response to Office Action," for Canadian Patent Application No. 3,079,289 filed with CIPO Sep. 23, 2021 (17 pages).
"Response to Non-Final Rejection," dated Jul. 12, 2021 for U.S. Appl. No. 16/167,140, submitted via EFS-Web on Oct. 12, 2021, 16 pages.
"Final Office Action," for U.S. Appl. No. 16/855,433 dated Feb. 1, 2022 (20 pages).
"Non-Final Office Action," for U.S. Appl. No. 16/167,079 dated Feb. 17, 2022 (37 pages).
"Non-Final Office Action," for U.S. Appl. No. 16/850,712 dated Jan. 21, 2022 (40 pages).
"Notice of Allowance," for U.S. Appl. No. 16/167,116 dated Jan. 26, 2022 (19 pages).
"Response to Communication Pursuant to Art. 94(3) EPC," for European Patent Application No. 18801137.3 filed Jan. 13, 2022 (8 pages).
"Response to Final Rejection," dated Dec. 27, 2021 for U.S. Appl. No. 16/167,140, submitted via EFS-Web on Feb. 9, 2022, 9 pages.
"Response to Final Rejection," dated Nov. 15, 2021 for U.S. Appl. No. 16/850,720, submitted via EFS-Web on Feb. 11, 2022, 12 pages.
"Response to Final Rejection," dated Nov. 5, 2021 and Advisory Action dated Feb. 9, 2022 for U.S. Appl. No. 16/855,421, submitted via EFS-Web on Mar. 4, 2022.
"Final Office Action," for U.S. Appl. No. 16/166,957 dated May 18, 2022 (35 pages).
"Final Office Action," for U.S. Appl. No. 16/167,079 dated May 27, 2022 (29 pages).
"Final Office Action," for U.S. Appl. No. 16/167,087 dated May 18, 2022 (26 pages).
"Non-Final Office Action," for U.S. Appl. No. 16/167,140 dated May 27, 2022 (25 pages).
"Non-Final Office Action," for U.S. Appl. No. 16/855,421 dated Jun. 7, 2022 (21 pages).
"Non-Final Office Action," for U.S. Appl. No. 16/855,433 dated May 27, 2022 (18 pages).
"Notice of Allowance," for U.S. Appl. No. 16/850,720 dated Apr. 14, 2022 (17 pages).
"Office Action," for Canadian Patent Application No. 3,079,213 dated Apr. 20, 2022 (6 pages).
"Office Action," for Canadian Patent Application No. 3,079,289 dated Mar. 24, 2022 (8 pages).
"Office Action," for Canadian Patent Application No. 3,079,314 dated Apr. 29, 2022 (3 pages).
"Office Action," for Canadian Patent Application No. 3,079,316 dated Jun. 3, 2022 (3 pages).
"Response to Communication Pursuant to Rules 161(1) and 162 EPC," for European Patent Application No. 20724332.0 filed May 11, 2022 (24 pages).
"Response to Communication Pursuant to Rules 161(1) and 162 EPC," for European Patent Application No. 20724702.4 filed May 11, 2022 (24 pages).
"Response to Communication Pursuant to Rules 161(1) and 162 EPC," for European Patent Application No. 20724703.2 filed Jun. 8, 2022 (12 pages).
"Response to Communication Pursuant to Rules 161(1) and 162 EPC," for European Patent Application No. 20727417.6 filed Jun. 1, 2022 (8 pages).

(56) References Cited

OTHER PUBLICATIONS

"Response to Communication Pursuant to Rules 161(1) and 162 EPC," for European Patent Application No. 20724333.8 filed Jun. 8, 2022 (8 pages).
"Response to Final Rejection," dated Dec. 27, 2021 and Advisory Action dated Mar. 9, 2022 for U.S. Appl. No. 16/167,140, submitted via EFS-Web on Mar. 25, 2022, 11 pages.
"Response to Final Rejection," dated Feb. 1, 2022 for U.S. Appl. No. 16/855,433, submitted via EFS-Web on May 2, 2022, 9 pages.
"Response to Non-Final Rejection," dated Dec. 22, 2021 for U.S. Appl. No. 16/166,957, submitted via EFS-Web on Mar. 22, 2022, 13 pages.
"Response to Non-Final Rejection," dated Dec. 22, 2021 for U.S. Appl. No. 16/167,087, submitted via EFS-Web on Mar. 22, 2022, 9 pages.
"Response to Non-Final Rejection," dated Feb. 17, 2022 for U.S. Appl. No. 16/167,079, submitted via EFS-Web on May 3, 2022, 11 pages.
"Response to Non-Final Rejection," dated Jan. 21, 2022 for U.S. Appl. No. 16/850,712, submitted via EFS-Web on Mar. 21, 2022, 10 pages.
"First Office Action," for Chinese Patent Application No. 201880068897.8 dated Sep. 21, 2022 (11 pages) with English Summary.
"Non-Final Office Action," for U.S. Appl. No. 16/850,712 dated Oct. 6, 2022 (11 pages).
"Non-Final Office Action," for U.S. Appl. No. 16/855,448 dated Nov. 7, 2022 (58 pages).
"Communication Pursuant to Article 94(3) EPC," for European Patent Application No. 18801138.1 dated Aug. 29, 2022 (5 pages).
"Decision of Rejection," for Japanese Patent Application No. 2020-542719 dated Oct. 19, 2021 (3 pages) No English Translation.
"Final Office Action," for U.S. Appl. No. 16/850,712 dated Jul. 5, 2022 (16 pages).
"International Preliminary Report on Patentability," for PCT Application No. PCT/US2021/019160 dated Sep. 9, 2022 (10 pages).
"International Search Report and Written Opinion," for PCT Application No. PCT/US2022/021161 dated Jun. 22, 2022 (15 pages).
"Non-Final Office Action," for U.S. Appl. No. 16/166,957 dated Sep. 29, 2022 (41 pages).
"Non-Final Office Action," for U.S. Appl. No. 16/167,087 dated Sep. 15, 2022 (24 pages).
Notice of Opposition for European Patent No. 3700627 filed Aug. 24, 2022 (20 pages).
"Office Action Response," for Canadian Patent Application No. 3,079,289 filed Jul. 18, 2022 (17 pages).
"Office Action Response," for Canadian Patent Application No. 3,079,314 filed Aug. 11, 2022 (7 pages).
"Response to Final Rejection," dated Jul. 5, 2022 and Advisory Action dated Sep. 15, 2022 for U.S. Appl. No. 16/850,712, submitted via EFS-Web on Sep. 23, 2022, 10 pages.
"Response to Final Rejection," dated Jul. 5, 2022 for U.S. Appl. No. 16/850,712, submitted via EFS-Web on Sep. 6, 2022, 10 pages.
"Response to Final Rejection," dated May 18, 2022 for U.S. Appl. No. 16/166,957, submitted via EFS-Web on Aug. 18, 2022, 14 pages.
"Response to Final Rejection," dated May 18, 2022 for U.S. Appl. No. 16/167,087, submitted via EFS-Web on Aug. 18, 2022, 9 pages.
"Response to Final Rejection," dated May 27, 2022 for U.S. Appl. No. 16/167,079, submitted via EFS-Web on Aug. 26, 2022, 12 pages.
"Response to Non-Final Rejection," dated Jun. 7, 2022 for U.S. Appl. No. 16/855,421, submitted via EFS-Web on Sep. 7, 2022, 9 pages.
"Response to Non-Final Rejection," dated May 27, 2022 for U.S. Appl. No. 16/167,140, submitted via EFS-Web on Aug. 25, 2022, 14 pages.
"Response to Non-Final Rejection," dated May 27, 2022 for U.S. Appl. No. 16/855,433, submitted via EFS-Web on Aug. 25, 2022, 9 pages.
"Response to Office Action," for Canadian Patent Application No. 3,079,213 filed Aug. 10, 2022 (10 pages).
"Third Office Action," for Japanese Patent Application No. 2020-542721 dated Aug. 23, 2022 (9 pages) with English translation.
Notice of Opposition for European Patent Application No. 18801134.0 on behalf of Novocure Gmbh, dated Jun. 28, 2022 (36 pages).
"Communication Pursuant to Article 94(3) EPC," for European Patent Application No. 20724333.8 dated Mar. 17, 2023 (6 pages).
"Decision of Rejection," for Japanese Patent Application No. 2021-562795 dated Mar. 28, 2023 (6 pages) with English translation.
"Final Office Action," for Japanese Patent Application No. 2020-542721 dated Mar. 7, 2023 (5 pages) with English translation.
"Final Office Action," for U.S. Appl. No. 16/166,957 dated Mar. 7, 2023 (49 pages).
"Final Office Action," for U.S. Appl. No. 16/167,087 dated Mar. 6, 2023 (30 pages).
"Final Office Action," for U.S. Appl. No. 16/855,433 dated May 3, 2023 (25 pages).
"First Office Action," for Chinese Patent Application No. 201880078118.2 dated Mar. 27, 2023 (17 pages) with English translation.
"International Search Report and Written Opinion," for PCT Application No. PCT/US2023/010469 dated Apr. 12, 2023 (19 pages).
"Non-Final Office Action," for U.S. Appl. No. 16/167,079 dated Mar. 23, 2023 (40 pages).
"Notice of Allowance," for U.S. Appl. No. 16/855,448 dated Mar. 8, 2023 (19 pages).
"Response to Communication Pursuant to Article 94(3) EPC," for European Patent Application No. 18800411.3 filed May 2, 2023 (11 pages).
"Response to Communication Pursuant to Article 94(3) EPC," for European Patent Application No. 18801138.1 filed Mar. 8, 2023 (10 pages).
"Response to Non-Final Rejection," dated Jan. 24, 2023 for U.S. Appl. No. 16/850,728, submitted via EFS-Web on Apr. 20, 2023, 8 pages.
"Response to Office Action," for Canadian Patent Application No. 3,079,213 filed Mar. 8, 2023 (6 pages).
"Response to Office Action," for Canadian Patent Application No. 3,079,289 filed Mar. 24, 2023 (18 pages).
"Second Office Action," for Chinese Patent Application No. 201880068897.8 dated Feb. 27, 2023 (9 pages) with English Summary.
"Communication Pursuant to Article 94(3) EPC," for European Patent Application No. 18800411.3 dated Dec. 22, 2022 (5 pages).
"Non-Final Office Action," for U.S. Appl. No. 16/167,140 dated Nov. 15, 2022 (29 pages).
"Non-Final Office Action," for U.S. Appl. No. 16/850,728 dated Jan. 24, 2023 (68 pages).
"Non-Final Office Action," for U.S. Appl. No. 16/855,433 dated Nov. 17, 2022 (39 pages).
"Notice of Allowance," for U.S. Appl. No. 16/850.712 dated Feb. 7, 2023 (14 pages).
"Notice of Allowance," for U.S. Appl. No. 16/855,421 dated Nov. 16, 2022 (17 pages).
"Office Action," for Canadian Patent Application No. 3,079,213 dated Dec. 5, 2022 (4 pages).
"Office Action," for Canadian Patent Application No. 3,079,289 dated Nov. 28, 2022 (7 pages).
"Office Action," for Japanese Patent Application No. 2021-562795 dated Nov. 15, 2022 (5 pages) with English Translation.
"Office Action," for Japanese Patent Application No. 2021-562797 dated Nov. 22, 2022 (9 pages), with English Translation.
"Office Action," for Japanese Patent Application No. 2021-562798 dated Nov. 15, 2022 (14 pages), with English translation.
"Office Action," for Japanese Patent Application No. 2021-562966 dated Nov. 29, 2022 (11 pages) with English Translation.
"Office Action," for Japanese Patent Application No. 2021-562972 dated Nov. 8, 2022 (26 pages) with English Translation.
"Response to Communication Pursuant to Rules 161(1) and 162 EPC," for European Patent Application No. 21712639.0 filed Jan. 20, 2023 (26 pages).

(56) References Cited

OTHER PUBLICATIONS

"Response to Non-Final Rejection," for U.S. Appl. No. 16/855,433, dated Nov. 17, 2022, submitted via EFS-Web on Feb. 17, 2023, 11 pages.

"Response to Non-Final Rejection," dated Nov. 15, 2022, based on U.S. Appl. No. 16/167,140, submitted via EFS- Web on Feb. 15, 2023, 12 pages.

"Response to Non-Final Rejection," dated Nov. 7, 2022 for U.S. Appl. No. 16/855,448, submitted via EFS-Web on Feb. 7, 2023, 9 pages.

"Response to Non-Final Rejection," dated Oct. 6, 2022 for U.S. Appl. No. 16/850,712, submitted via EFS-Web on Jan. 4, 2023, 10 pages.

"Response to Non-Final Rejection," dated Sep. 15, 2022 for U.S. Appl. No. 16/167,087, submitted via EFS-Web on Dec. 13, 2022, 8 pages.

"Response to Non-Final Rejection," dated Sep. 29, 2022 for U.S. Appl. No. 16/166,957, submitted via EFS-Web on Dec. 13, 2022, 16 pages.

"Communication Pursuant to Article 94(3) EPC," for European Patent Application No. 18801138.1 dated Jul. 7, 2023 (5 pages).

"Decision of Rejection," for Japanese Patent Application No. 2021-562797 dated May 16, 2023 (10 pages), with English translation.

"Final Office Action," for U.S. Appl. No. 16/850,728 dated Jun. 26, 2023 (26 pages).

"Office Action," for Canadian Patent Application No. 3,079,289 dated Jul. 6, 2023 (3 pages).

"Office Action," for Japanese Patent Application No. 2021-562972 dated May 5, 2023 (12 pages), with English translation.

"Response to Communication Pursuant to Article 94(3) EPC," for European Patent Application No. 20724333.8 filed Jul. 25, 2023 (28 pages).

"Response to Final Rejection," dated May 3, 2023, for U.S. Appl. No. 16/855,433, submitted via EFS-Web on Aug. 2, 2023, 10 pages.

"Response to Non-Final Rejection," dated Mar. 23, 2023 for U.S. Appl. No. 16/167,079, submitted via EFS-Web on Jun. 23, 2023, 12 pages.

"Second Office Action," for Japanese Patent Application No. 2021-562966 dated Jun. 13, 2023 (9 pages), with English translation.

"Third Office Action," for Chinese Patent Application No. 201880068897.8 dated Jun. 9, 2023 (10 pages) with English Summary.

"Final Office Action," for U.S. Appl. No. 16/167,140 dated May 24, 2023 (41 pages).

"First Office Action," for Chinese Patent Application No. 201880068852.0 dated Mar. 15, 2023 (9 pages).

"Response to Final Rejection," dated Mar. 6, 2023 for U.S. Appl. No. 16/167,087, submitted via EFS-Web on Jun. 6, 2023, 10 pages.

"Response to Final Rejection," dated Mar. 7, 2023 for U.S. Appl. No. 16/166,957, submitted via EFS-Web on Jun. 7, 2023, 18 pages.

"Second Office Action," for Japanese Patent Application No. 2021-562798 dated May 9, 2023 (11 pages) with English translation.

\* cited by examiner

SYSTEMS AND METHODS FOR TREATMENT OF PANCREATIC CANCER

This application claims the benefit of U.S. Provisional Application No. 62/890,811, filed Feb. 24, 2020, the content of which is herein incorporated by reference in its entirety.

FIELD

Embodiments herein relate to medical devices and methods for using the same to treat cancerous tumors within a bodily tissue. More specifically, embodiments herein relate to using medical devices configured to generate therapeutic electric fields at the site of a pancreatic cancerous tumor.

BACKGROUND

According to the American Cancer Society, cancer accounts for nearly 25% of the deaths that occur in the United States each year. The current standard of care for cancerous tumors can include first-line therapies such as surgery, radiation therapy, and chemotherapy. Additional second-line therapies can include radioactive seeding, cryotherapy, hormone or biologics therapy, ablation, and the like. Combinations of first-line therapies and second-line therapies can also be a benefit to patients if one particular therapy on its own is not effective.

Cancerous tumors can form if one normal cell in any part of the body mutates and then begins to grow and multiply too much and too quickly. Cancerous tumors can be a result of a genetic mutation to the cellular DNA or RNA that arises during cell division, an external stimulus such as ionizing or non-ionizing radiation, exposure to a carcinogen, or a result of a hereditary gene mutation. Regardless of the etiology, many cancerous tumors are the result of unchecked rapid cellular division.

The pancreas releases enzymes that aid digestion and produces hormones that help to manage blood sugar. Pancreatic cancer begins in the tissues of the pancreas. Pancreatic cancer can develop from two kinds of cells in the pancreas: exocrine cells and neuroendocrine cells, such as islet cells. The exocrine type is more common and is usually found at an advanced stage. Pancreatic neuroendocrine tumors (islet cell tumors) are less common.

Mitosis is the process of cellular division that is a part of the cell cycle for all somatic cells in the body, including many types of cancerous cells. Mitosis includes four basic phases: prophase, metaphase, anaphase, and telophase. Just prior to prophase, a cell will copy its chromosomes to create two identical sister chromatids. During prophase, the chromosomes start to condense and the nuclear membrane surrounding the nucleus disappears. The mitotic spindle also begins to form during prophase.

The mitotic spindle includes a self-organized bipolar array of microtubules and centrosomes. Microtubules are generally formed from the polymerization of the highly polar alpha-tubulin and beta-tubulin proteins. Centrosomes are similarly protein-based organelles, two of which migrate to opposite sides of the dividing cell at this phase. The negatively charged end of the microtubules attach to the centrosomes. The positively charged end of the microtubules radiate toward the equator of the dividing cell where they eventually attach to a kinetochore of each sister chromatid.

Metaphase can be defined by all chromosomes being aligned at the equator of the dividing cell and bound in the mitotic spindle. An equal number of sister chromatids are then pulled toward opposite ends of the cell during anaphase. Once all chromosomes have been separated, the process of telophase begins, where the cell membrane begins to form a cleavage furrow between the two newly forming sister cells, and cell division becomes complete once the cells physically separate from one another in a process called cytokinesis.

SUMMARY

Embodiments herein relate to medical devices and methods for using the same to treat cancerous tumors within a bodily tissue. In a first aspect, a medical device system is included having an electric field generating circuit configured to generate one or more electric fields, and control circuitry in communication with the electric field generating circuit. The control circuitry can be configured to control delivery of the one or more electric fields from the at least one electric field generating circuit. The system can include one or more electrodes disposed on a first stimulation lead to deliver the electric fields to a site of a cancerous tumor within a patient and one or more electrodes disposed on a second stimulation lead to deliver the electric fields to the site of a cancerous tumor within a patient. The first and second stimulation leads can be configured to be implanted on or about a duodenum. The control circuitry can be configured to cause the electric field generating circuit to generate one or more electric fields at frequencies selected from a range of between 10 kHz to 1 MHz.

In a second aspect, in addition to one or more of the preceding or following aspects, or in the alternative to some aspects, the first stimulation lead can be configured to be affixed to an anterior exterior surface of the duodenum and the second stimulation lead is configured to be affixed to a posterior exterior surface of the duodenum.

In a third aspect, in addition to one or more of the preceding or following aspects, or in the alternative to some aspects, at least one of the first and second stimulation leads can include one or more thermal shielding pads disposed thereon.

In a fourth aspect, in addition to one or more of the preceding or following aspects, or in the alternative to some aspects, the thermal shielding pads are configured to pivot around the first or second stimulation lead.

In a fifth aspect, in addition to one or more of the preceding or following aspects, or in the alternative to some aspects, at least one of the first and second stimulation leads can include one or more electrical field blocking pads disposed thereon.

In a sixth aspect, in addition to one or more of the preceding or following aspects, or in the alternative to some aspects, the electrical field blocking pads can include at least one of a metal grid and a metalized material.

In a seventh aspect, in addition to one or more of the preceding or following aspects, or in the alternative to some aspects, the system further can include one or more attachment anchors disposed along the first or second stimulation lead.

In an eighth aspect, in addition to one or more of the preceding or following aspects, or in the alternative to some aspects, the attachment anchors are configured to pivot around the first or second stimulation lead.

In a ninth aspect, in addition to one or more of the preceding or following aspects, or in the alternative to some aspects, they system further can include a housing, the control circuitry disposed within the housing.

In a tenth aspect, in addition to one or more of the preceding or following aspects, or in the alternative to some aspects, the electrodes on the first stimulation lead or the electrodes on the second stimulation lead are arranged in a grid.

In an eleventh aspect, in addition to one or more of the preceding or following aspects, or in the alternative to some aspects, the system can include four or more electrodes disposed on the first stimulation lead to deliver the electric fields to a site of the cancerous tumor within the patient and four or more electrodes disposed on the second stimulation lead to deliver the electric fields to a site of the cancerous tumor within the patient.

In a twelfth aspect, a method of treating pancreatic cancer is included, the method including positioning a first electrical stimulation lead on or about a posterior exterior surface of a duodenum of a patient, positioning a second electrical stimulation lead on or about an anterior exterior surface of the duodenum of the patient, and generating an electrical field between at least one pair of electrodes disposed on the electrical stimulation leads, the electric field having frequencies within a range of between 10 kHz to 1 MHz.

In a thirteenth aspect, in addition to one or more of the preceding or following aspects, or in the alternative to some aspects, the method further can include suturing the first electrical stimulation lead and the second electrical stimulation lead to the duodenum.

In a fourteenth aspect, in addition to one or more of the preceding or following aspects, or in the alternative to some aspects, the method further can include positioning one or more thermal shielding pads about at least one of the first and second stimulation leads.

In a fifteenth aspect, in addition to one or more of the preceding or following aspects, or in the alternative to some aspects, the thermal shielding pads can be configured to pivot around the first or second stimulation lead.

In a sixteenth aspect, in addition to one or more of the preceding or following aspects, or in the alternative to some aspects, the method further can include positioning one or more electrical field blocking pads about at least one of the first and second stimulation leads.

In a seventeenth aspect, in addition to one or more of the preceding or following aspects, or in the alternative to some aspects, the electrical field blocking pads can include at least one of a metal grid and a metalized material.

In an eighteenth aspect, in addition to one or more of the preceding or following aspects, or in the alternative to some aspects, one or more attachment anchors disposed along the first or second stimulation lead.

In a nineteenth aspect, in addition to one or more of the preceding or following aspects, or in the alternative to some aspects, the attachment anchors can be configured to pivot around the first or second stimulation lead.

In a twentieth aspect, in addition to one or more of the preceding or following aspects, or in the alternative to some aspects, the electrodes on the first stimulation lead or the electrodes on the second stimulation lead can be arranged in a grid pattern.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following figures (FIGS.), in which.

Figure 1:
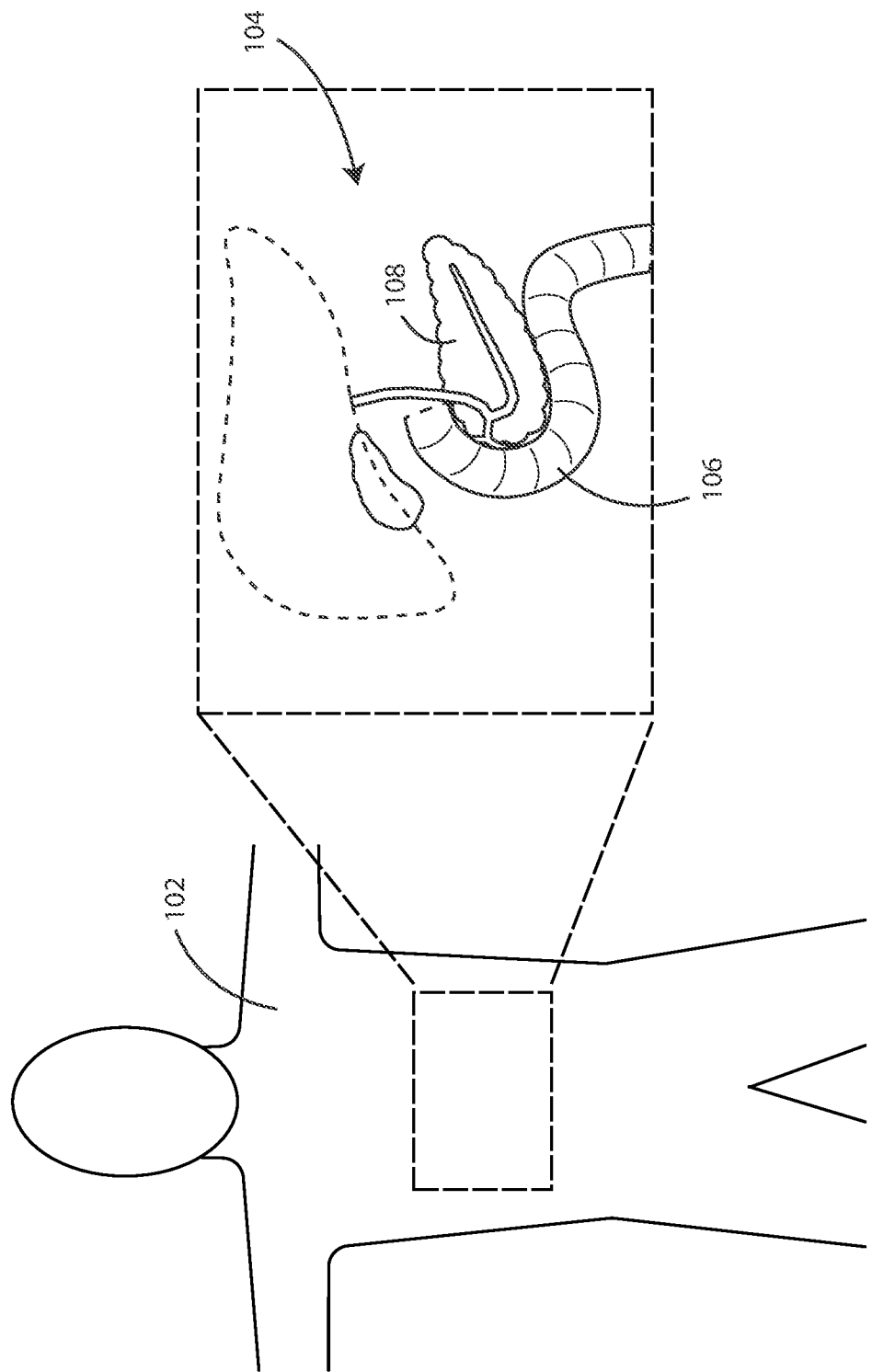
FIG. 1 is a schematic view of a patient in accordance with various embodiments herein.

While embodiments are susceptible to various modifications and alternative forms, specifics thereof have been shown by way of example and drawings, and will be described in detail. It should be understood, however, that the scope herein is not limited to the particular aspects described. On the contrary, the intention is to cover modifications, equivalents, and alternatives falling within the spirit and scope herein.

DETAILED DESCRIPTION

As referenced above, many cancerous tumors can result from unchecked rapid cellular division. Some traditional first-line therapies to treat cancerous tumors can include surgery, radiation therapy, and chemotherapy. However, many first-line therapies have undesirable concomitant side effects, such as fatigue, hair loss, immunosuppression, and long surgical recovery times, to name a few.

While not intending to be bound by theory, it is believed that alternating electric fields can disrupt mitosis within a cancerous tumor by interfering with the dipole alignment of key proteins involved in cellular division; tubulin and septin in particular. The polymerization of tubulin proteins that form microtubule spindle fibers can be disrupted, thus preventing the formation of spindle fibers required for chromosome separation. This can halt cellular division at the metaphase stage of mitosis. In some instances an alternating electric field can halt polymerization of already growing spindle fibers, leading to incomplete spindles and unequal chromosome separation during anaphase, should the cell survive that long. In each case, halting microtubule spindle formation and unequal chromosome separation during anaphase caused by incomplete polymerization of microtubules can result in apoptosis (i.e., programmed cell death).

It is also believed that alternating electric fields can lead to increased electric field density near the cleavage furrow of the dividing cells during telophase. An increased electric field density in the region of the cleavage furrow can result in dielectrophoresis of charged macromolecules, such as proteins and nucleic acids, toward the high electric field density at the furrow. The unequal concentration of key macromolecules required for cellular division at the site of the cleavage furrow can disrupt the final separation of the sister cells during telophase and eventually lead to apoptosis.

The small intestine or small bowel is an organ in the gastrointestinal tract where most of the end absorption of nutrients and minerals from food takes place. The duodenum is the first part of the small intestine immediately beyond the stomach, leading to the jejunum.

The duodenum has a "C" shape and curves around and outlines the head of the pancreas. In accordance with embodiments herein, electrical stimulation leads can be implanted on or about the duodenum following the "C" shape. This provides an ideal position for the leads to deliver electrical fields to the site of a cancerous tumor within the pancreas of a patient and therefore treat pancreatic cancer.

Figure 2:
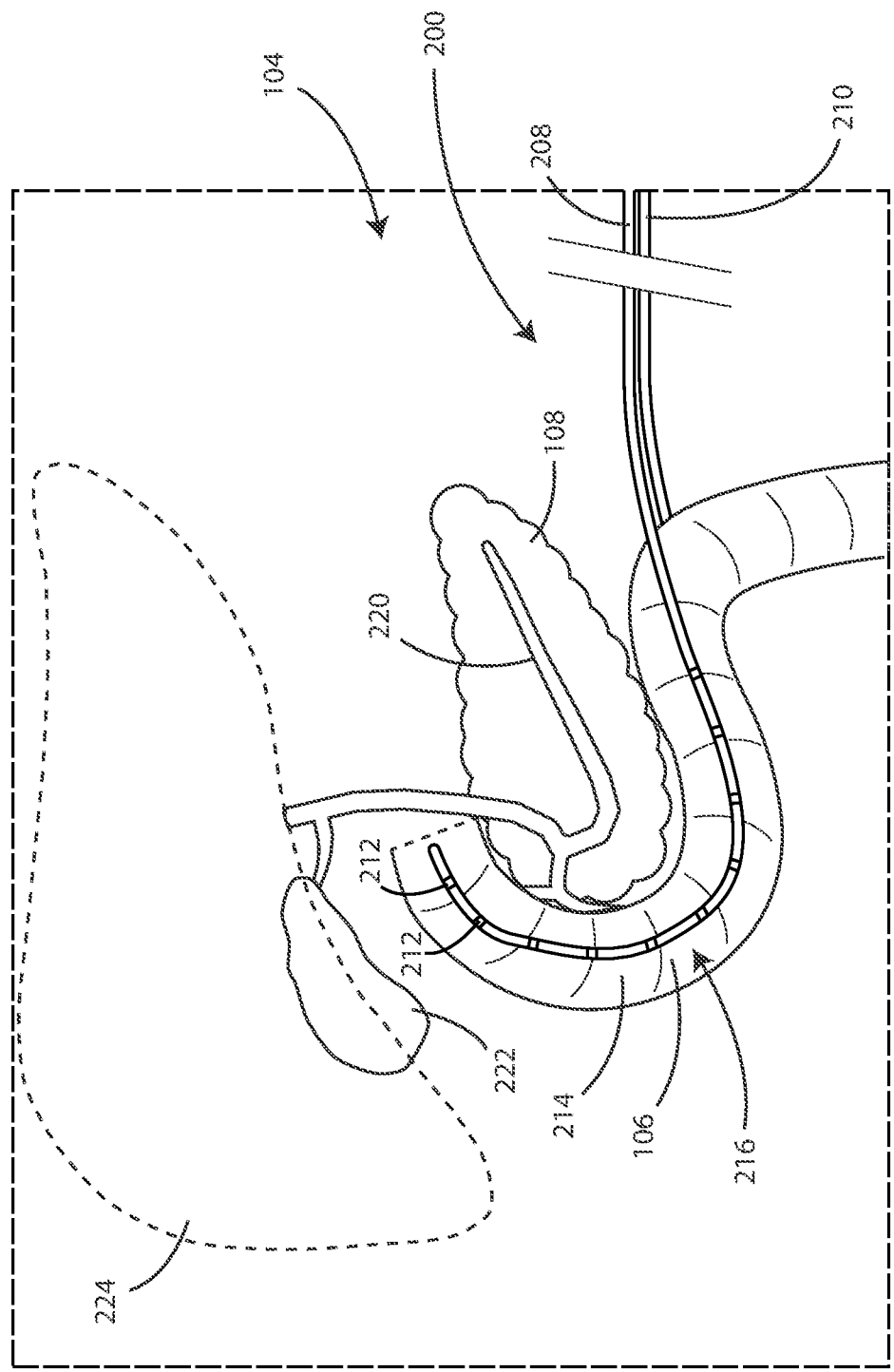
FIG. 2 is a schematic view of a medical device system in accordance with various embodiments herein.

Referring now to FIG. 1, a schematic view of a patient 102 is shown in accordance with various embodiments herein. The patient 102 has internal organs 104. The internal organs 104 shown include a duodenum 106 and a pancreas 108. Referring now to FIG. 2, a schematic view of a medical device system 200 is shown in accordance with various embodiments herein. The internal organs 104 shown in this view include the duodenum 106, pancreas 108, pancreatic duct 220, gallbladder 222, and liver 224. The duodenum 106 includes an anterior surface 214 and a posterior surface (not shown in this view).

The medical device system 200 also includes a first stimulation lead 208 and a second stimulation lead 210. The medical device system 200 can include at least one electric field generating circuit configured to generate one or more electric fields, and control circuitry in communication with the electric field generating circuit. The control circuitry can be configured to control delivery of the one or more electric fields from the at least one electric field generating circuit.

In various embodiments, the first stimulation lead 208 and the second stimulation lead 210 can be used to deliver the electric fields to the site of a cancerous tumor within a patient. The first stimulation lead 208 can include a first plurality of electrodes 212. The number of electrodes on the first stimulation lead 208 can vary. In some embodiments, the first stimulation lead 208 can include 1, 2, 3, 4, 5, 6, 7, 8, 10, 12, 15, 20, 25, 30, 40, or more electrodes, or a number of electrodes falling within a range between any of the foregoing. The first stimulation lead 208 can also include a curved portion 216. The degree of curvature can be about 30, 35, 40, 45, 50, 55, 60, 65, 70, 80, 90, 100, 110, 120, 130, 140, 160, 180, 200, 220, 240, 260, 280, 300, 320, 340, or 360 or more, or an amount of curvature falling within a range between any of the foregoing. Similarly, the second stimulation lead 210 can a plurality of electrodes and a curved portion (not shown in this view). The number of electrodes on the second stimulation lead 210 can be the same or different as the number of electrodes on the first stimulation lead 208. It will be appreciated that more than a first stimulation lead and second stimulation lead can be used in the embodiments herein. Further, in some embodiments, only a single stimulation may be used.

The electrodes can take on many different forms and configurations. In some embodiments, the electrodes can be spaced out along an electrical stimulation lead. In some embodiments, the electrodes on at least one of the first stimulation lead or the electrodes on the second stimulation lead can be arranged in a grid pattern. Many different materials can be used to form the electrodes. In some embodiments, the electrodes can include a conductive metal. In some embodiments, the electrodes can include one or more of stainless steel, iridium oxide, platinum, aluminum, or the like.

In some embodiments, the first stimulation lead 208 can be configured to be affixed to or otherwise positioned adjacent to an anterior exterior surface of the duodenum 106. For example, the first stimulation lead 208 can be sutured to the duodenum 106. In some cases, the first stimulation lead 208 can be otherwise attached to the duodenum 106 such as with staples, clips, bands, medical adhesive, or the like. Similarly, the second stimulation lead 210 is configured to be affixed to or otherwise positioned adjacent to a posterior exterior surface of the duodenum 106.

Figure 3:
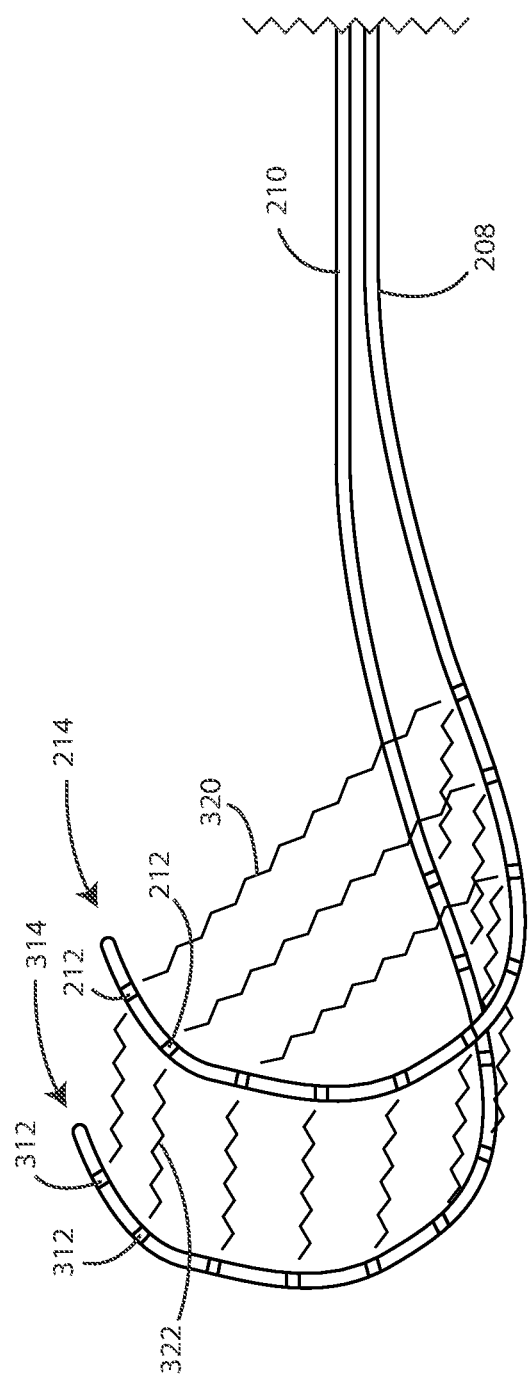
FIG. 3 is a schematic view of electrical stimulation leads in accordance with various embodiments herein.

Referring now to FIG. 3, a schematic view of electrical stimulation leads is shown in accordance with various embodiments herein. As referenced before, the duodenum (not shown in this view) can include an anterior surface 214 and a posterior surface 314. A medical device system (not shown in this view) includes a first stimulation lead 208 with electrodes 212 disposed thereon. The medical device system also includes a second stimulation lead 210 with a second set of electrodes 312 disposed thereon.

Electric fields can be generated between pairs of electrodes. For example, electrical fields can be generated between pairs of electrodes disposed on the same lead or pairs of electrodes with electrodes disposed on separate leads. As illustrated in FIG. 3, electric fields can be generated along at least a first vector 320. The electric fields can also be generated along at least a second vector 322. In some embodiments, the vectors can be at least partially perpendicular to one another. However, it will be appreciated that in practice, many different vectors can be used (e.g., beyond just two). In addition, embodiments herein include more than just those with two electrical stimulation leads. For example, embodiments herein can include those with 1, 2, 3, 4, 5, 6, 7, or 8 or more electrical stimulation leads.

Figure 4:
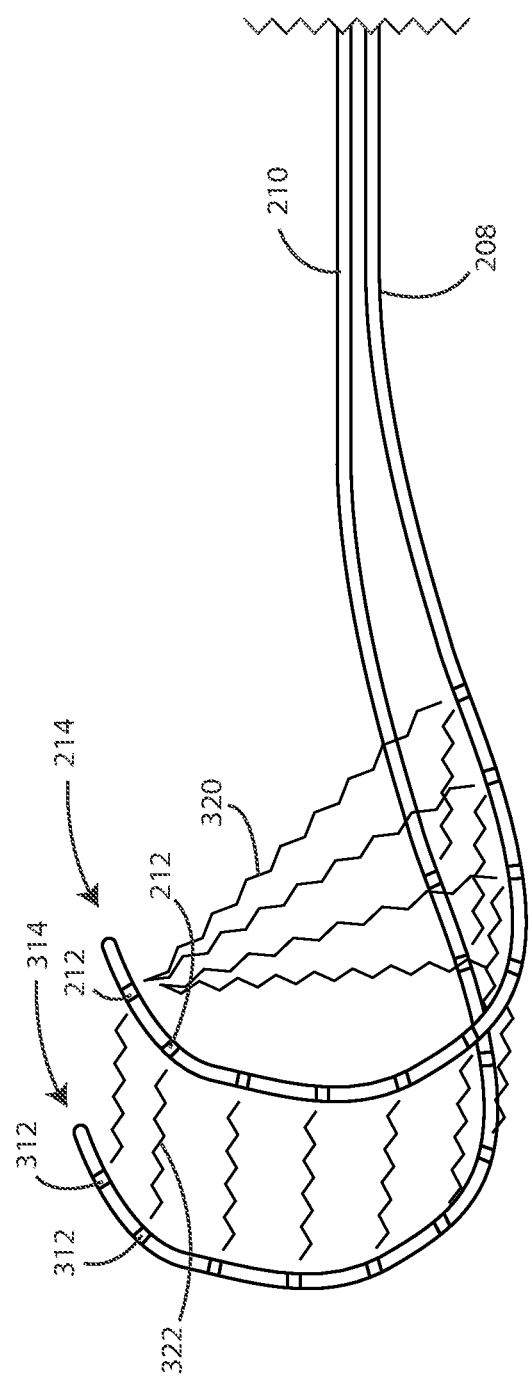
FIG. 4 is a schematic view of electrical stimulation leads in accordance with various embodiments herein.

Vectors for electrical stimulation herein can be complex and include more than 1 to 1 relationships of electrodes. For example, a single electrode may pair with multiple ground electrodes creating a dense and complex electrical stimulation field. Referring now to FIG. 4, a schematic view of electrical stimulation leads is shown in accordance with various embodiments herein. FIG. 4 is generally similar to FIG. 3. However, in FIG. 4, vector 320 is part of a one to many relationship between electrodes for generating an electrical field.

Figure 5:
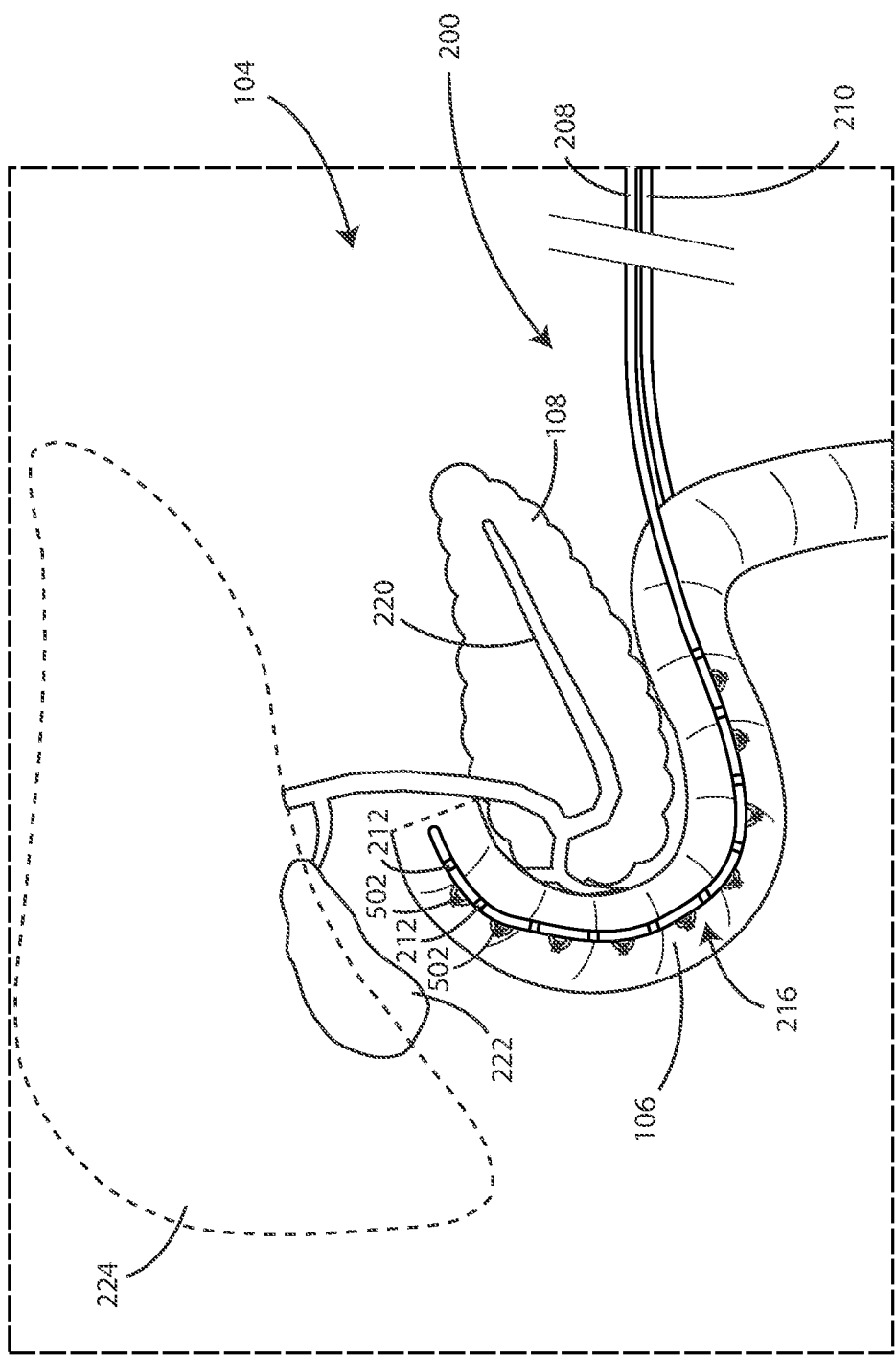
FIG. 5 is a schematic view of a medical device system in accordance with various embodiments herein.

It can be useful to secure the electrical stimulation leads within a given position in the abdominal cavity. This can be accomplished in many different ways. In some embodiments, suture anchors or other can be disposed on the electrical stimulation leads to assist in securing the electrical stimulation leads. Referring now to FIG. 5, a schematic view of a medical device system 200 is shown in accordance with various embodiments herein. The internal organs 104 shown here include a duodenum 106, pancreas 108, pancreatic duct 220, gallbladder 222 and liver 224. The medical device system 200 also includes a first stimulation lead 208 with electrodes 212 disposed thereon. The first stimulation lead 208 also includes a curved portion 216. Similarly, the medical device system 200 also includes a second stimulation lead 210, which can also include electrodes disposed thereon.

In various embodiments, attachment anchors 502 can be disposed along the first stimulation lead 208 or the second stimulation lead 210. In some embodiments, the attachment anchors 502 can define apertures such as to allow for suturing. In some embodiments, the attachment anchors 502 can take other shapes or forms. The attachment anchors 502 can take on the form of posts, arms, hooks, hoops, or the like.

In some embodiments, the attachment anchors 502 can be configured to pivot around the first stimulation lead 208 or second stimulation lead 210. For example, the attachment anchors can include an aperture through which the electrical stimulation lead can pass but not be bonded thereto.

As referenced above, attachment anchors can take on many different shapes or forms. In some embodiments, the attachment anchors can take on the form of loops or partial loops. In some embodiments, attachment anchors can include relatively flat portions or pads that can be configured to directly interface with a surface of the duodenum.

Figure 6:
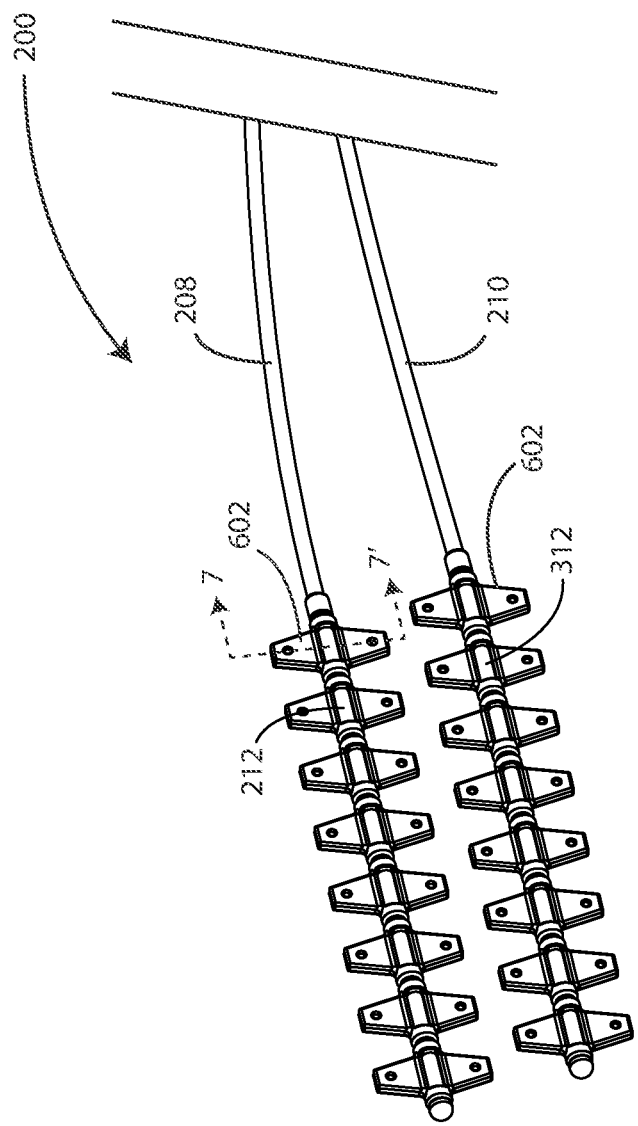
FIG. 6 is a schematic view of a medical device system in accordance with various embodiments herein.

Referring now to FIG. 6, a schematic view of a medical device system 200 is shown in accordance with various embodiments herein. As before, the medical device system includes a first stimulation lead 208 with electrodes 212 and surface contact members 602, which can serve as a form of attachment anchor. The medical device system also includes a second stimulation lead 210 including a second set of electrodes 312 and surface contact members 602.

Figure 7:
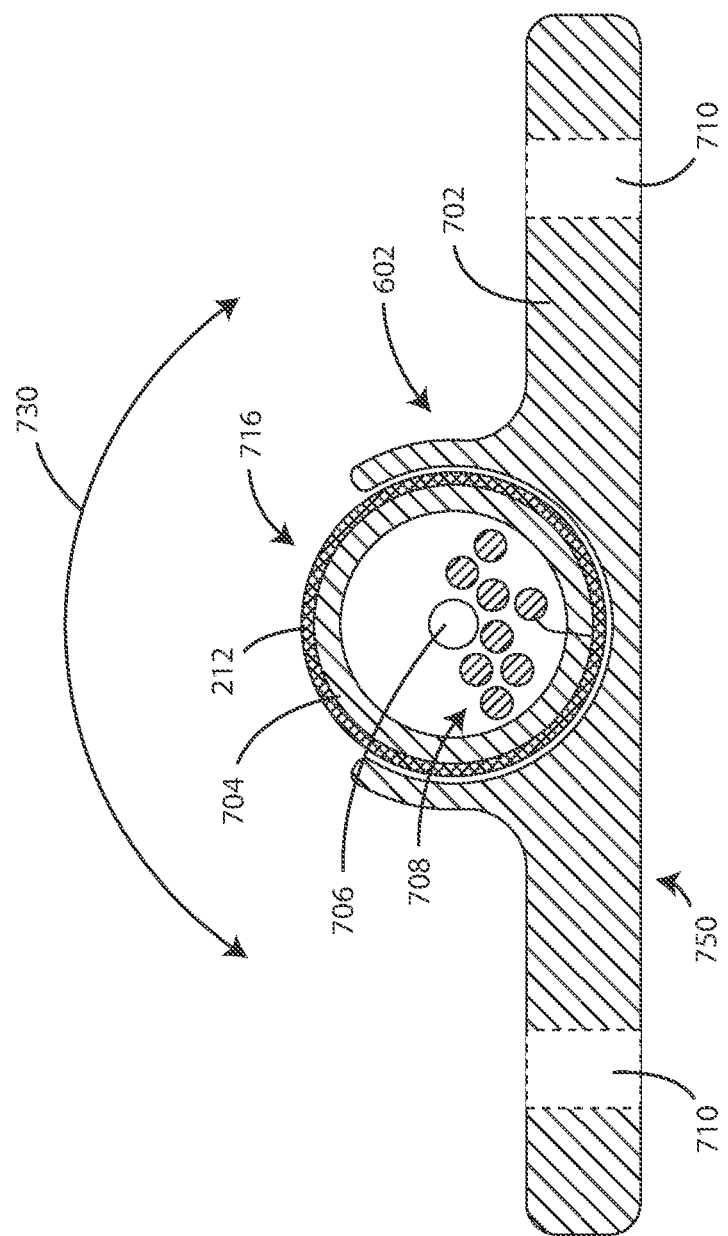
FIG. 7 is a cross-sectional view of a portion of an electrical stimulation lead as taken along line 6-6' in accordance with various embodiments herein.

Referring now to FIG. 7, a cross-sectional view of a portion of an electrical stimulation lead as taken along line 7-7' of FIG. 6 is shown in accordance with various embodiments herein. A stimulation lead passes through a surface contact member 602. The stimulation lead includes a lead body 704, an electrode 212 (such as a ring electrode) disposed on the lead body 704, and (optionally) a guidewire lumen 706 disposed in the lead body. The first stimulation lead also includes electrical conductors 708 disposed therein. At least one electrical conductor 708 can be in electrical communication with the electrode 212.

The surface contact member 602 includes contact member body 702 and suture apertures 710 disposed therein. The contact member body 702 can include a surface 750 therein configured for contact with a surface of the duodenum. The surface 750 can be flat or slightly curved (such as concave). In some embodiments, the contact member body 702 can be made of a flexible material such that the surface 750 can bend in order to provide a good fit against curving surface of the duodenum. The size of the surface (or width of the surface) can vary. In some embodiments, the surface 750 has a width that is at least about 1.5, 2, 3, 4, 5, 6, 7, 8, or 10 times the width (or diameter) of the stimulation lead, or an amount falling within a range between any of the foregoing.

The surface contact member 602 can include a window 716 (or aperture or opening) so as to expose at least a portion of the electrode 212. The window 716 can be disposed on a side of the surface contact member 602 that is opposite from the surface 750 (or contact surface). In some embodiments, the window 716 can expose at least about 5, 10, 15, 20, 25, 30, 40, 50, 60, 70, 80, 90, 100, 120, 140, 160 or more degrees of the circumference of the electrode 212, or an amount falling within a range between any of the foregoing. In some embodiments, the window 716 has a width that is less than the diameter of the stimulation lead in order to hold the same within the surface contact member 602.

The surface contact member 602 can be configured to pivot 730 about the stimulation leads. In some embodiments, the surface contact member 602 can fit tightly with the stimulation lead such that it will pivot about the stimulation lead, but retain its position if force is not applied.

Figure 8:
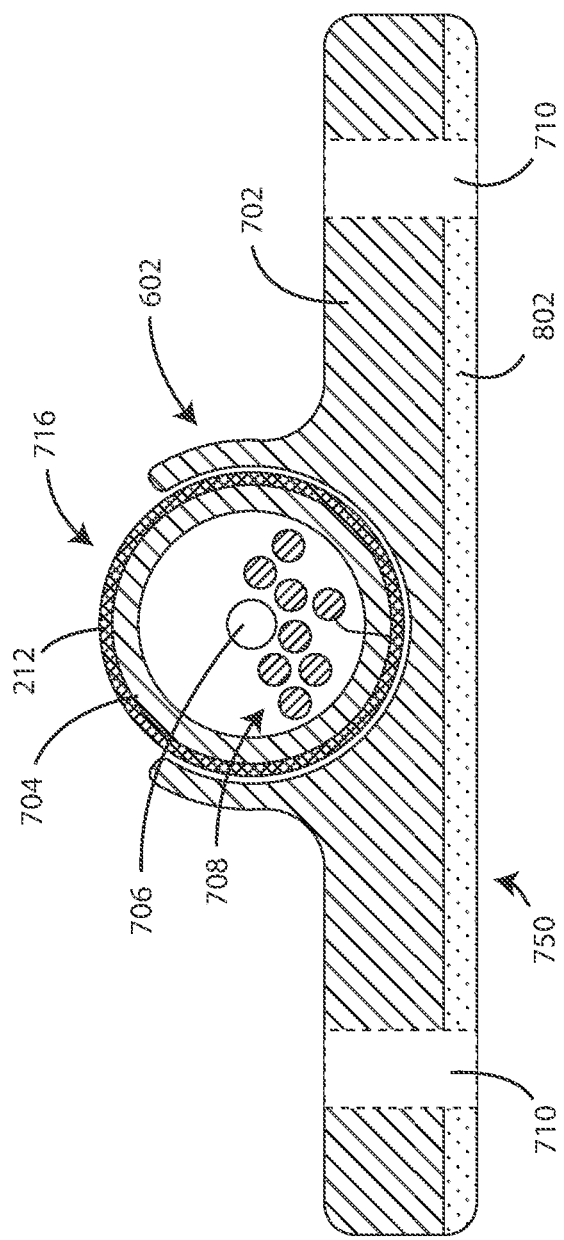
FIG. 8 is a cross-sectional view of a portion of an electrical stimulation lead as taken along line 6-6' in accordance with various embodiments herein.

Referring now to FIG. 8, a cross-sectional view of a portion of an electrical stimulation lead as taken along line 7-7' of FIG. 6 is shown in accordance with various embodiments herein. A stimulation lead passes through a surface contact member 602. The stimulation lead includes a lead body 704, an electrode 212 (such as a ring electrode) disposed on the lead body 704, and (optionally) a guidewire lumen 706 disposed in the lead body. The first stimulation lead also includes electrical conductors 708 disposed therein. At least one electrical conductor 708 can be in electrical communication with the electrode 212. The surface contact member 602 includes contact member body 702 and suture apertures 710 disposed therein.

It can be beneficial to shield the duodenum from heat generated as part of the generation of electrical stimulation. As such, in some embodiments, thermal shielding pads 802 can be included to shield the duodenum and/or other tissues from thermal damage. In various embodiments, the thermal shielding pads 802 can be configured to pivot around the first or second stimulation lead 210 as the surface contact members 602 pivot. The thermal shielding pads 802 can be made of various materials. In some embodiments, the thermal shielding pads 802 can formed of a polymer. In some embodiments, the thermal shielding pads 802 can be formed of a metal, a composite, a ceramic, or the like. In some embodiments, the thermal shielding pads 802 can be porous and in other embodiment non-porous.

Figure 9:
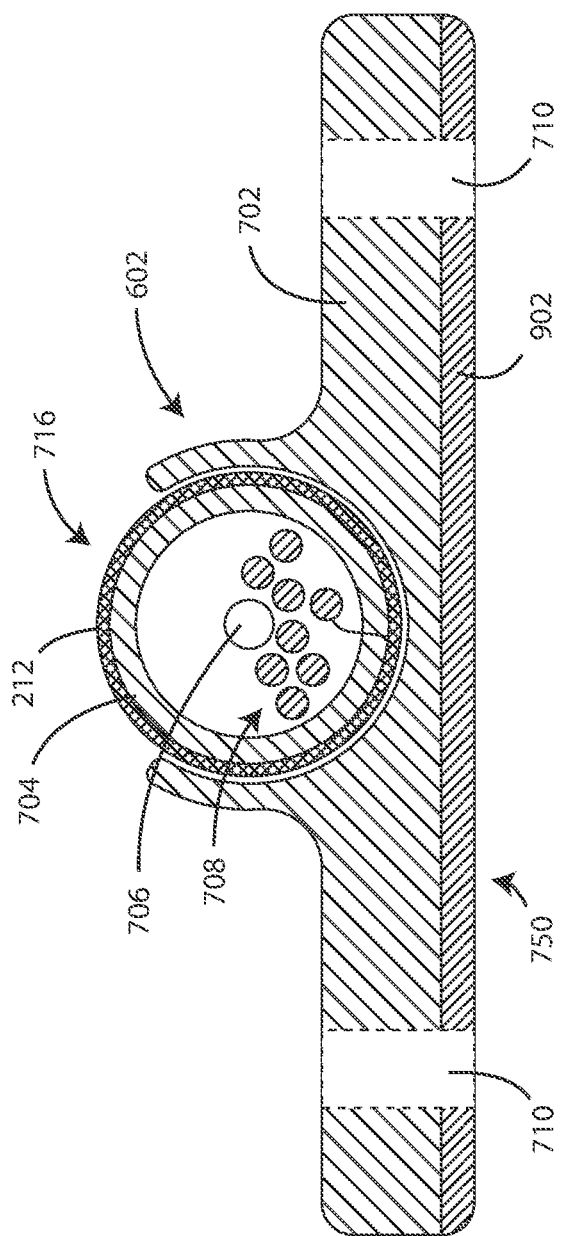
FIG. 9 is a cross-sectional view of a portion of an electrical stimulation lead as taken along line 6-6' in accordance with various embodiments herein.

Referring now to FIG. 9, a cross-sectional view of a portion of an electrical stimulation lead as taken along line 7-7' of FIG. 6 is shown in accordance with various embodiments herein. As before, a stimulation lead passes through a surface contact member 602. The stimulation lead includes a lead body 704 and a guidewire lumen 706 disposed therein. The first stimulation lead also includes electrical conductors 708 disposed therein. The surface contact member 602 includes contact member body 702 and suture apertures 710 disposed therein.

It can also be beneficial to shield the duodenum from electrical stimulation. As such, in some embodiments, electrical field blocking pads 902 can be included to shield the duodenum and/or other tissues from electrical stimulation/ electrical fields. In various embodiments, the electrical field blocking pads 902 can be configured to pivot around the first or second stimulation lead 210 as the surface contact members 602 pivot.

In various embodiments, the electrical field blocking pads 902 can include a metal. In various embodiments, the electrical field blocking pads 902 can include at least one of a metal grid, a wire grid, a metal sheet, and a metalized material.

Figure 10:
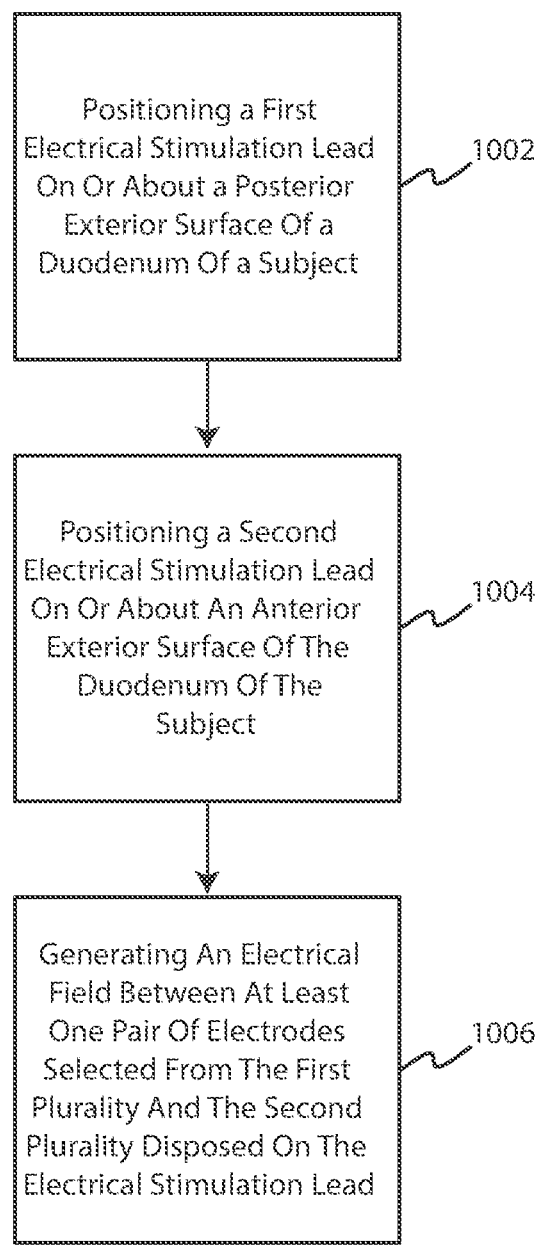
FIG. 10 is a flow chart of a method in accordance with various embodiments herein.

Referring now to FIG. 10, a flow chart of a method is shown in accordance with various embodiments herein. The method can include an operation of positioning 1002 a first electrical stimulation lead on or about a posterior exterior surface of a duodenum of a patient, the first electrical stimulation lead comprising a first plurality of electrodes disposed thereon. The method can include an operation of positioning 1004 a second electrical stimulation lead on or about an anterior exterior surface of the duodenum of the patient, the second electrical stimulation lead comprising a second plurality of electrodes disposed thereon. The method can include an operation of generating 1006 an electrical field between at least one pair of electrodes selected from the first plurality and the second plurality disposed on the electrical stimulation lead, the electric field having frequencies within a range of between 10 kilohertz (kHz) to 1 megahertz (MHz) or higher.

Embodiments of systems and devices herein can include those that are entirely implanted as well as those that have both implanted and external components.

Figure 11:
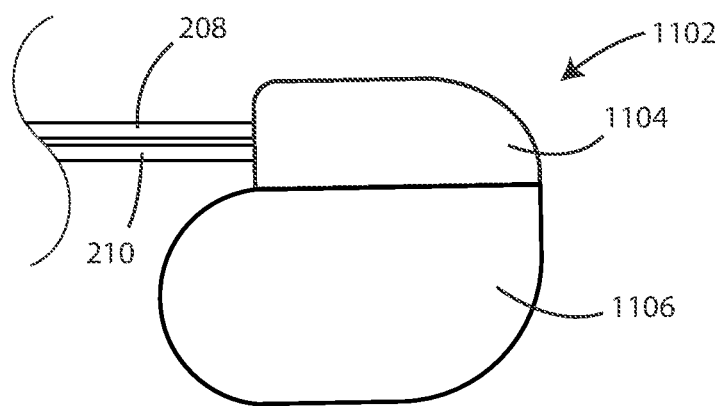
FIG. 11 is a schematic view of a medical device in accordance with various embodiments herein.

Referring now to FIG. 11, a schematic cross-sectional view of exemplary medical device 1102 is shown in accordance with various embodiments herein. In this example, the medical device 1102 can be an implantable medical device. It will be appreciated that the features of medical device 1102 can be included in any of the medical devices described herein. The medical device 1102 can include header 1104 and implantable housing 1106. The first stimulation lead 208 and the second stimulation lead 210 can connect to the header 1104. Circuitry and other components for operation of the medical device 1102 can be disposed within the housing 206 and/or the header 204. The medical device 1102 can be implanted within a patient in various places such as within the abdomen, in a subpectoral position, a submammary position, or the like.

Figure 12:
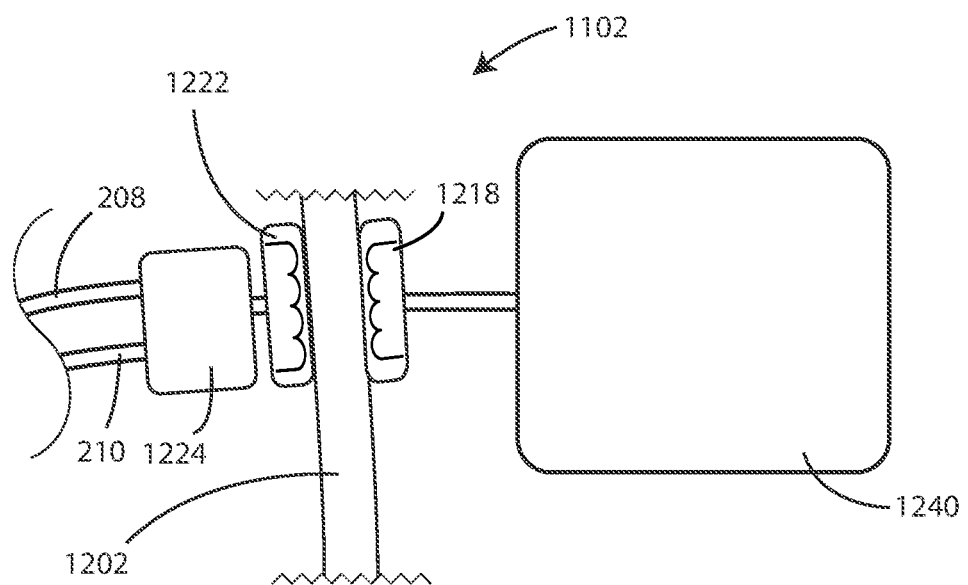
FIG. 12 is a schematic view of a medical device in accordance with various embodiments herein.

However, in some embodiments herein, only some components of the system may be implanted. For example, referring now to FIG. 12, an embodiment is shown with some implanted components and some external components. In this specific example, the medical device 1102 can include an external power supply unit 1240 that is disposed outside of the dermis 1202 of a subject. The external power supply unit 1240 can be connected to a wireless power transmission device or antenna 1218. The medical device 1102 can also include a wireless power receiving device or antenna 1222. Power can be exchanged wirelessly in various ways including, but not limited to, via induction. In some embodiments, the medical device 1102 can include an internal control unit 1224 (that can include various circuitry and other components for operation of the medical device such as elements described further below). The internal control unit 1224 can be connected to the first stimulation lead 208 and the second stimulation lead 210.

Figure 13:
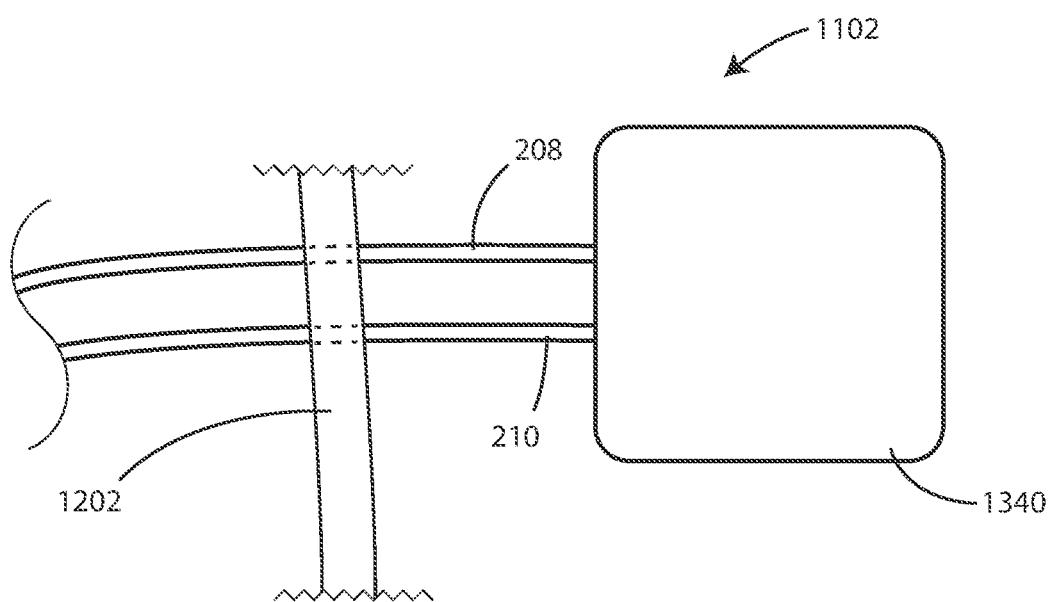
FIG. 13 is a schematic view of a medical device in accordance with various embodiments herein.

In some embodiments, components of the system can pass through the dermis of the patient. For example, referring now to FIG. 13, an embodiment is shown with at least some components passing through the dermis 1202 of the subject. In this specific example, the medical device 1102 can include an external power and control unit 1340 that is disposed outside of the dermis 1202 of a subject. The external power and control unit 1340 can be connected to the first stimulation lead 208 and the second stimulation lead 210. The first stimulation lead 208 and the second stimulation lead 210 can pass through the dermis 1202 of the subject.

Figure 14:
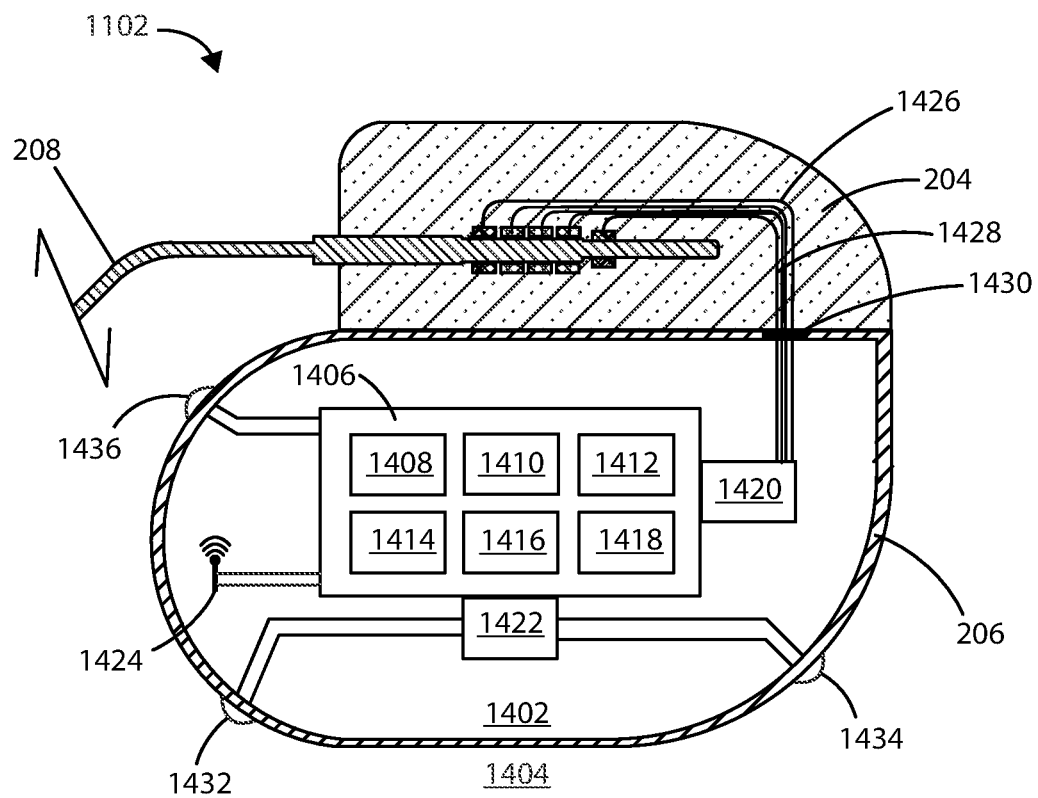
FIG. 14 is a schematic cross-sectional view of medical device in accordance with various embodiments herein.

Referring now to FIG. 14, a schematic cross-sectional view of an exemplary medical device 1102 is shown in accordance with various embodiments herein. The components shown therein can be a part of various devices herein whether implanted or external. Housing 206 can define an interior volume 1402 that can be hollow and that in some embodiments is hermetically sealed off from the area 1404 outside of medical device 202. In some embodiments the housing 206 can be filled with components and/or structural materials such that it is non-hollow. The medical device 1102 can include control circuitry 1406, which can include various components 1408, 1410, 1412, 1414, 1416, and 1418 disposed within housing 206. In some embodiments, these components can be integrated and in other embodiments these components can be separate. In yet other embodiments, there can be a combination of both integrated and separate components. The medical device 202 can also include an antenna 1424, to allow for unidirectional or bidirectional wireless data communication. In some embodiments, the components of medical device 202 can include an inductive energy receiver coil (not shown) communicatively coupled or attached thereto to facilitate transcutaneous recharging of the medical device via recharging circuitry.

The various components 1408, 1410, 1412, 1414, 1416, and 1418 of control circuitry 1406 can include, but are not limited to, a microprocessor, memory circuit (such as random access memory (RAM) and/or read only memory (ROM)), recorder circuitry, controller circuit, a telemetry circuit, a power supply circuit (such as a battery), a timing circuit, and an application specific integrated circuit (ASIC), a recharging circuit, amongst others. Control circuitry 1406 can be in communication with an electric field generating circuit 1420 that can be configured to generate electric current to create one or more electric fields. The electric field generating circuit 1420 can be integrated with the control circuitry 1406 or can be a separate component from control circuitry 1406. Control circuitry 1406 can be configured to control delivery of electric current from the electric field generating circuit 1420. In some embodiments, the electric field generating circuit 1420 can be present in a portion of the medical device that is external to the body.

In some embodiments, the control circuitry 1406 can be configured to direct the electric field generating circuit 1420 to deliver an electric field using one or more frequencies selected from a range of within 10 kHz to 1 MHz or higher. In some embodiments, the control circuitry 1406 can be configured to direct the electric field generating circuit 1420 to deliver an electric field at one or more frequencies selected from a range of within 100 kHz to 500 kHz. In some embodiments, the control circuitry 1406 can be configured to direct the electric field generating circuit 1420 to deliver an electric field at one or more frequencies selected from a range of within 100 kHz to 300 kHz. In some embodiments, the control circuitry 1406 can be configured to direct the electric field generating circuit 1420 to periodically deliver an electric field using one or more frequencies greater than 1 MHz.

In some embodiments, the electric field can be effective in disrupting cellular mitosis in cancerous cells. The electric field can be delivered to the site of a cancerous tumor along more than one vector. In some examples, the electric field can be delivered along at least one vector, including at least one of the lead electrodes. In some embodiments, at least two vectors with spatial diversity between the two vectors can be used. The vectors can be spatially separated (e.g., the vectors can be disposed at an angle with respect to one another) by at least about 10, 20, 30, 40, 50, 60, 70, 80 or 90 degrees.

A desired electric field strength can be achieved by delivering an electric current between two electrodes. The specific current and voltage at which the electric field is delivered can vary and can be adjusted to achieve the desired electric field strength at the site of the tissue to be treated. In some embodiments, the control circuitry 1406 can be configured to direct the electric field generating circuit 1420 to deliver an electric field using currents ranging from 1 milliamp (mAmp) to 1000 mAmp to the site of a cancerous tumor. In some embodiments, the control circuitry 1406 can be configured to direct the electric field generating circuit 1420 to deliver an electric field using currents ranging from 20 mAmp to 500 mAmp to the site of a cancerous tumor. In some embodiments, the control circuitry 1406 can be configured to direct the electric field generating circuit 1420 to deliver an electric field using currents ranging from 30 mAmp to 300 mAmp to the site of a cancerous tumor.

In some embodiments, the control circuitry 1406 can be configured to direct the electric field generating circuit 1420 to deliver an electric field using currents including 1 mAmp, 2 mAmp, 3 mAmp, 4 mAmp, 5 mAmp, 6 mAmp, 7 mAmp, 8 mAmp, 9 mAmp, 10 mAmp, 15 mAmp, 20 mAmp, 25 mAmp, 30 mAmp, 35 mAmp, 40 mAmp, 45 mAmp, 50 mAmp, 60 mAmp, 70 mAmp, 80 mAmp, 90 mAmp, 100 mAmp, 125 mAmp, 150 mAmp, 175 mAmp, 200 mAmp, 225 mAmp, 250 mAmp, 275 mAmp, 300 mAmp, 325 mAmp, 350 mAmp, 375 mAmp, 400 mAmp, 425 mAmp, 450 mAmp, 475 mAmp, 500 mAmp, 525 mAmp, 550 mAmp, 575 mAmp, 600 mAmp, 625 mAmp, 650 mAmp, 675 mAmp, 700 mAmp, 725 mAmp, 750 mAmp, 775 mAmp, 800 mAmp, 825 mAmp, 850 mAmp, 875 mAmp, 900 mAmp, 925 mAmp, 950 mAmp, 975 mAmp, or 1000 mAmp. It will be appreciated that the control circuitry can be configured to direct the electric field generating circuit 1420 to deliver an electric field at a current falling within a range, wherein any of the forgoing currents can serve as the lower or upper bound of the range, provided that the lower bound of the range is a value less than the upper bound of the range.

In some embodiments, the control circuitry 1406 can be configured to direct the electric field generating circuit 1420 to deliver an electric field using voltages ranging from 1 root-mean-square voltage ($V_{rms}$) to 50 $V_{rms}$ to the site of a cancerous tumor. In some embodiments, the control circuitry 1406 can be configured to direct the electric field generating circuit 1420 to deliver an electric field using voltages ranging from 5 $V_{rms}$ to 30 $V_{rms}$ to the site of a cancerous tumor. In some embodiments, the control circuitry 1406 can be configured to direct the electric field generating circuit 1420 to deliver an electric field using voltages ranging from 10 $V_{rms}$ to 20 $V_{rms}$ to the site of a cancerous tumor.

In some embodiments, the control circuitry 1406 can be configured to direct the electric field generating circuit 1420 to deliver an electric field using one or more voltages including 1 $V_{rms}$, 2 $V_{rms}$, 3 $V_{rms}$, 4 $V_{rms}$, 5 $V_{rms}$, 6 $V_{rms}$, 7 $V_{rms}$, 8 $V_{rms}$, 9 $V_{rms}$, 10 $V_{rms}$, 15 $V_{rms}$, 20 $V_{rms}$, 25 $V_{rms}$, 30 $V_{rms}$, 35 $V_{rms}$, 40 $V_{rms}$, 45 $V_{rms}$, or 50 $V_{rms}$. It will be appreciated that the control circuitry can be configured to direct the electric field generating circuit 1420 to deliver an electric field using a voltage falling within a range, wherein any of the forgoing voltages can serve as the lower or upper bound of the range, provided that the lower bound of the range is a value less than the upper bound of the range.

In some embodiments, the control circuitry 1406 can be configured to direct the electric field generating circuit 1420 to deliver and electric field using one or more frequencies including 10 kHz, 20 kHz, 30 kHz, 40 kHz, 50 kHz, 60 kHz, 70 kHz, 80 kHz, 90 kHz, 100 kHz, 125 kHz, 150 kHz, 175 kHz, 200 kHz, 225 kHz, 250 kHz, 275 kHz, 300 kHz, 325 kHz, 350 kHz, 375 kHz, 400 kHz, 425 kHz, 450 kHz, 475 kHz, 500 kHz, 525 kHz, 550 kHz, 575 kHz, 600 kHz, 625 kHz, 650 kHz, 675 kHz, 700 kHz, 725 kHz, 750 kHz, 775 kHz, 800 kHz, 825 kHz, 850 kHz, 875 kHz, 900 kHz, 925 kHz, 950 kHz, 975 kHz, 1 MHz. It will be appreciated that the electric field generating circuit 1420 can deliver an electric field using a frequency falling within a range, wherein any of the foregoing frequencies can serve as the upper or lower bound of the range, provided that the upper bound is greater than the lower bound.

In some embodiments, the control circuitry 1406 can be configured to direct the electric field generating circuit 1420 to generate one or more applied electric field strengths selected from a range of within 0.25 volts per centimeter (V/cm) to 1000 V/cm. In some embodiments, the control circuitry 1406 can be configured to direct the electric field generating circuit 1420 to generate one or more applied electric field strengths of greater than 3 V/cm. In some embodiments, the control circuitry 1406 can be configured to direct the electric field generating circuit 1420 to generate one or more applied electric field strengths selected from a range of within 1 V/cm to 10 V/cm. In some embodiments, the control circuitry 1406 can be configured to direct the electric field generating circuit 1420 to generate one or more applied electric field strengths selected from a range of within 3 V/cm to 5 V/cm.

In other embodiments, the control circuitry 1406 can be configured to direct the electric field generating circuit 1420 to generate one or more applied electric field strengths including 0.25 V/cm, 0.5 V/cm, 0.75 V/cm, 1.0 V/cm, 2.0 V/cm, 3.0 V/cm, 5.0 V/cm, 6.0 V/cm, 7.0 V/cm, 8.0 V/cm, 9.0 V/cm, 10.0 V/cm, 20.0 V/cm, 30.0 V/cm, 40.0 V/cm, 50.0 V/cm, 60.0 V/cm, 70.0 V/cm, 80.0 V/cm, 90.0 V/cm, 100.0 V/cm, 125.0 V/cm, 150.0 V/cm, 175.0 V/cm, 200.0 V/cm, 225.0 V/cm, 250.0 V/cm, 275.0 V/cm, 300.0 V/cm, 325.0 V/cm, 350.0 V/cm, 375.0 V/cm, 400.0 V/cm, 425.0 V/cm, 450.0 V/cm, 475.0 V/cm, 500.0 V/cm, 600.0 V/cm, 700.0 V/cm, 800.0 V/cm, 900.0 V/cm, 1000.0 V/cm. It will be appreciated that the electric field generating circuit 1420 can generate an electric field having a field strength at a treatment site falling within a range, wherein any of the foregoing field strengths can serve as the upper or lower bound of the range, provided that the upper bound is greater than the lower bound.

In some embodiments, the control circuitry 1406 can be configured to direct the electric field generating circuit 1420 to deliver an electric field via leads 208, 210 to the site of a cancerous tumor located within a bodily tissue. In other embodiments, the control circuitry 1406 can be configured to direct the electric field generating circuit 1420 to deliver an electric field via the housing 206 of medical device 202 to the site of a cancerous tumor located within a bodily tissue. In other embodiments, the control circuitry 1406 can be configured to direct the electric field generating circuit 1420 to deliver an electric field between leads 208, 210 and the housing 206 of medical device 202. In some embodiments, one or more leads 208, 210 can be in electrical communication with the electric field generating circuit 1420. In some embodiments, the one or more leads 208, 210 can include one or more electrodes (212 and 312, respectively as shown, e.g., in FIGS. 3 & 6) disposed along the length of the leads 208, 210, where the electrodes 212 and 312 can be in electrical communication with the electric field generating circuit 1420.

In some embodiments, various components within medical device 202 can include an electric field sensing circuit 1422 configured to generate a signal corresponding to sensed electric fields. Electric field sensing circuit 1422 can be integrated with control circuitry 1406 or it can be separate from control circuitry 1406.

Sensing electrodes can be disposed on or adjacent to the housing of the medical device, on one or more leads connected to the housing, on a separate device implanted near or in the tumor, or any combination of these locations. In some embodiments, the electric field sensing circuit 1422 can include a first sensing electrode 1432 and a second sensing electrode 1434. In other embodiments, the housing 206 itself can serve as a sensing electrode for the electric field sensing circuit 1422. The electrodes 1432 and 1434 can be in communication with the electric field sensing circuit 1422. The electric field sensing circuit 1422 can measure the electrical potential difference (voltage) between the first electrode 1432 and the second electrode 1434. In some embodiments, the electric field sensing circuit 1422 can measure the electrical potential difference (voltage) between the first electrode 1432 or second electrode 1434, and an electrode disposed along the length of one or more leads 208, 210. In some embodiments, the electric field sensing circuit can be configured to measure sensed electric fields and to record electric field strength in V/cm.

It will be appreciated that the electric field sensing circuit 1422 can additionally measure an electrical potential difference between the first electrode 1432 or the second electrode 1434 and the housing 206 itself. In other embodiments, the medical device can include a third electrode 1436, which can be an electric field sensing electrode or an electric field generating electrode. In some embodiments, one or more sensing electrodes can be disposed along an electrical stimulation lead and can serve as additional locations for sensing an electric field. Many combinations can be imagined for measuring electrical potential difference between electrodes disposed along the length of one or more leads 208, 210 and the housing 206 in accordance with the embodiments herein. It will be appreciated that field sensing electrodes and field generating electrodes herein can be one in the same in various embodiments.

In some embodiments, one or more leads (such as 208 or 210) can be in electrical communication with the electric field generating circuit 1420. The one or more leads 208, 210 can include one or more electrodes. As discussed above, it will be appreciated that the one or more electrodes 212 and 312 as shown in FIGS. 2-6 can be any combination of electric field sensing electrodes or electric field generating electrodes, depicted as 1508 and 1512 and described in reference to FIG. 11. In some embodiments, various electrical conductors, such as electrical conductors 1426 and 1428, can pass from the header 204 through a feed-through structure 1430 and into the interior volume 1402 of medical device 202. As such, the electrical conductors 1426 and 1428 can serve to provide electrical communication between the one or more leads 208, 210 and control circuitry 1406 disposed within the interior volume 1402 of the housing 206.

In some embodiments, recorder circuitry can be configured to record the data produced by the electric field sensing circuit 1422 and record time stamps regarding the same. In some embodiments, the control circuitry 1406 can be hardwired to execute various functions, while in other embodiments the control circuitry 1406 can be directed to implement instructions executing on a microprocessor or other external computation device. A telemetry circuit can also be provided for communicating with external computation devices such as a programmer, a home-based unit, and/or a mobile unit (e.g. a cellular phone, personal computer, smart phone, tablet computer, and the like).

Figure 15:
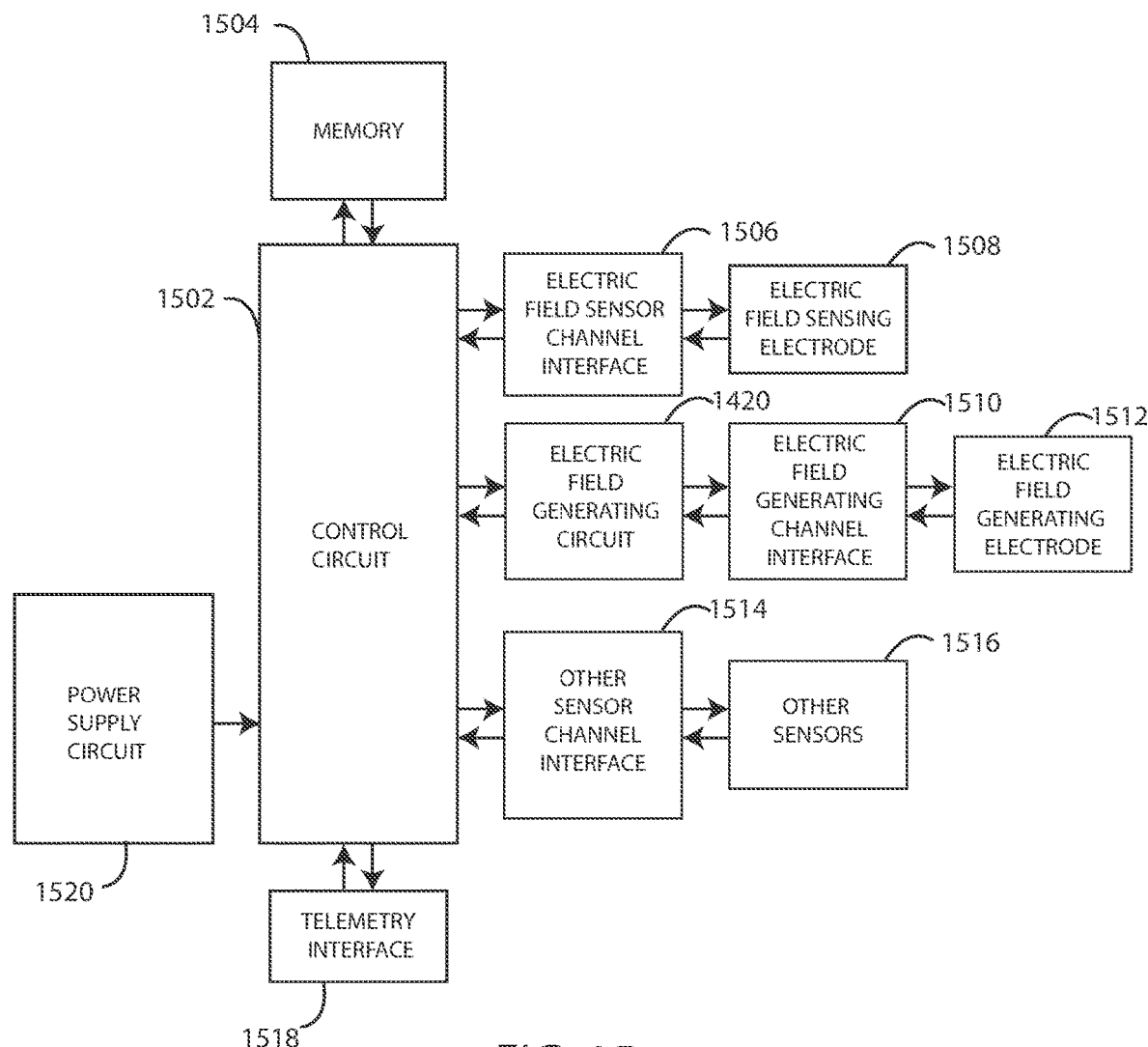
FIG. 15 is a schematic diagram of components of a medical device in accordance with various embodiments herein.

Elements of various embodiments of the medical devices described herein are shown in FIG. 15. However, it will be appreciated that some embodiments can include additional elements beyond those shown in FIG. 15. In addition, some embodiments may lack some elements shown in FIG. 15. The medical devices as embodied herein can gather information through one or more sensing channels and can output information through one or more field generating channels. A microprocessor 1502 can communicate with a memory 1504 via a bidirectional data bus. The microprocessor 1502 can be in electric communication with power supply circuit 1520. The memory 1504 can include read only memory (ROM) or random access memory (RAM) for program storage and RAM for data storage. The microprocessor 1502 can also be connected to a telemetry interface 1518 for communicating with external devices such as a programmer, a home-based unit and/or a mobile unit (e.g. a cellular phone, personal computer, smart phone, tablet computer, and the like) or directly to the cloud or another communication network as facilitated by a cellular or other data communication network. In some embodiments, the medical device can include an inductive energy receiver coil interface (not shown) communicatively coupled or attached thereto to facilitate transcutaneous recharging of the medical device.

The medical devices herein can include one or more electric field sensing electrodes 1508 and one or more electric field sensor channel interfaces 1506 that can communicate with a port of microprocessor 1502. The medical devices can also include one or more electric field generating electrodes 1512 and one or more electric field generating channel interfaces 1510 and one or more electric field generating circuits 1420 that can communicate with a port of microprocessor 1502. The medical devices can also include one or more other sensors 1516, such as physiological sensors, respiration sensors, or chemical sensors, and one or more other sensor channel interfaces 1514 that can communicate with a port of microprocessor 1502. The channel interfaces 1506, 1510, and 1514 can include various components such as analog-to-digital converters for digitizing signal inputs, sensing amplifiers, registers which can be written to by the control circuitry in order to adjust the gain and threshold values for the sensing amplifiers, source drivers, modulators, demodulators, multiplexers, and the like.

In some embodiments, the medical devices herein can include an electric field generating circuit configured to generate one or more electric fields at or near a site of the cancerous tumor. The medical devices herein can include control circuitry in communication with the electric field generating circuit, the control circuitry configured to control delivery of the one or more electric fields from the electric field generating circuit at or near the site of the cancerous tumor. The control circuitry can cause the electric field generating circuit to generate one or more electric fields at frequencies selected from a range of between 10 kHz to 1 MHz at the site of a cancerous tumor located within a bodily tissue, the one or more electric fields effective to delay mitosis and cause mitotic synchronization within a proportion of the cancerous cell population. In some embodiments, the medical device further can include one or more electrical leads in electrical communication with the electric field generating circuit.

In some embodiments, the medical devices herein include a medical device system for treating a cancerous tumor. The medical device housing can include an electric field generating circuit configured to generate one or more electric fields at or near a site of the cancerous tumor, the cancerous tumor including a cancerous cell population. The medical device system can include control circuitry in communication with the electric field generating circuit, where the control circuitry is configured to control delivery of the one or more electric fields from the electric field generating circuit at or near the site of the cancerous tumor. The medical device system can include a drug delivery catheter for administering one or more chemotherapeutic agents at or near the site of the cancerous tumor. The control circuitry of the medical device system causes the electric field generating circuit to generate one or more electric fields at frequencies selected from a range of between 10 kHz to 1 MHz at the site of a cancerous tumor located within a bodily tissue, the one or more electric fields effective to delay mitosis and cause mitotic synchronization within a proportion of the cancerous cell population.

In some embodiments, the medical devices herein can include a medical device for treating a cancerous tumor located within a patient. The medical device can include an electric field generating circuit configured to generate one or more electric fields at or near a site of the cancerous tumor, the cancerous tumor including a cancerous cell population. The medical device can include control circuitry in communication with the electric field generating circuit. The control circuitry of the medical device controls delivery of the one or more electric fields from the electric field generating circuit at or near the site of the cancerous tumor by following a predefined schedule that causes the electric fields to vary in at least one of intensity and frequency over the course of a defined time period of at least six hours.

The medical devices herein can include a medical device for of treating a cancerous tumor, including one or more implantable electrodes configured for placement on the inside of a body of a patient with the cancerous tumor. The medical device can include one or more external electrodes configured for placement on an outside surface of the body of the patient. The medical device can include an electric field generating circuit configured for generating an electric field between at least one pair of electrodes according to a predefined schedule, the electric field having frequencies within a range of between 10 kHz to 1 MHz. The medical device can include control circuitry configured for receiving a pause command from the patient, wherein the pause command causes cessation of generating the electric field.

Applied Electric Fields

The electric fields applied to the cancerous tumors using the methods herein can be applied using a variety of modalities. Exemplary therapeutic parameter sets can include those that implement the following concepts: sweeping through a range of frequencies; stacking of one or more frequencies simultaneously; stepping through one or more frequencies sequentially; the spatial or temporal delivery of one or more electric fields; sweeping through a range of electric field strengths; applying an effective rotating electric field; modulating a voltage control mode or a current control mode; implementing one or more duty cycles; pulse width modulation; manipulation of the electrical waveform shape and/or pulse sequence; and the occasional use of high frequency or high electric fields strength pulses.

The therapeutic parameter sets can be programmed into a medical device to operate autonomously, or they can be queried and manipulated by the patient or a clinician using an external computation device such as a programmer, a home-based unit, and/or a mobile unit (e.g. a cellular phone, personal computer, smart phone, tablet computer, and the like). In other embodiments, the therapeutic parameter sets can be wirelessly communicated to the medical device from an external computation device. Frequencies and/or electric field strengths suitable for use in any of the therapeutic parameter sets herein are discussed above with respect to electric field generating circuit. In some embodiments, one or more therapeutic parameter sets can be implemented simultaneously. In other embodiments, one or more therapeutic parameter sets can be implemented in an alternating fashion.

Figure 16:
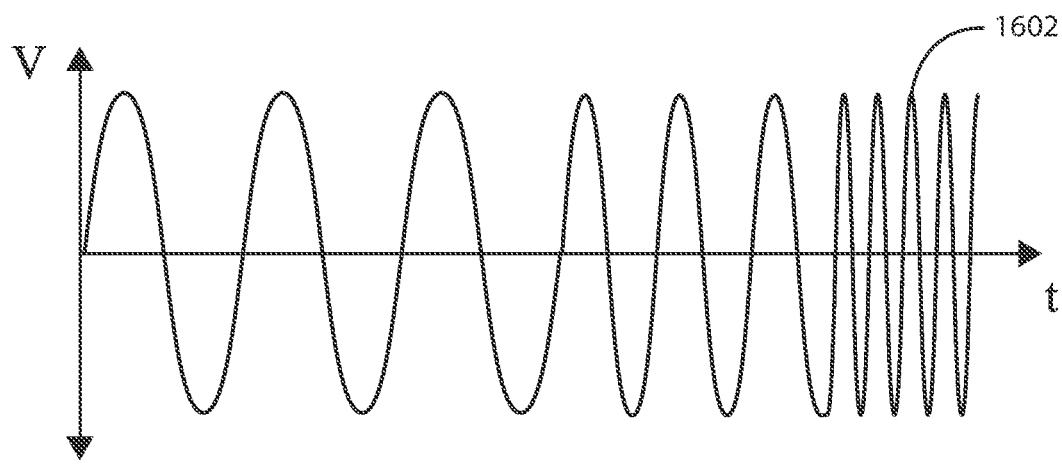
FIG. 16 is a plot of an exemplary electric field in accordance with various embodiments herein.
Figure 17:
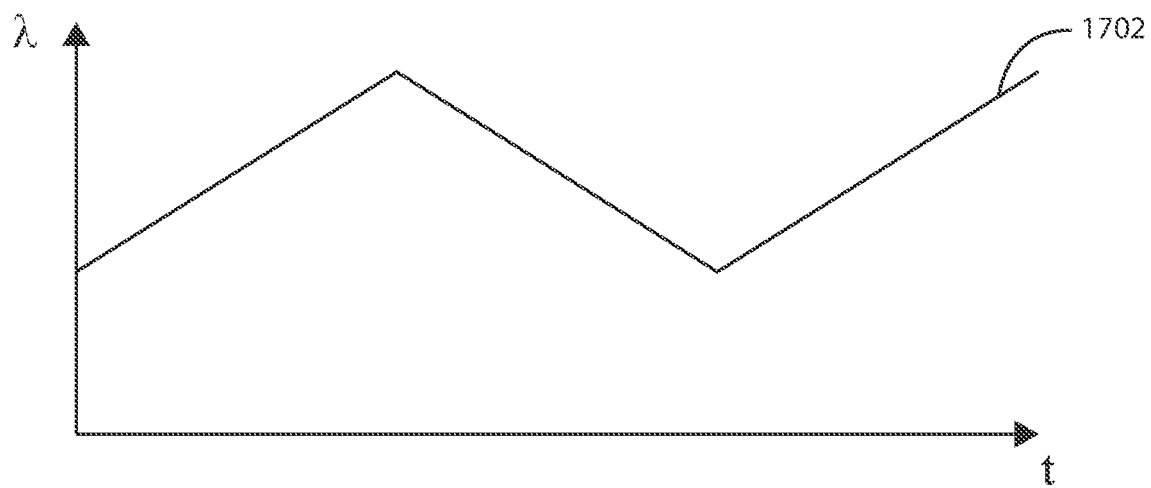
FIG. 17 is a plot of an exemplary electric field in accordance with various embodiments herein.

By way of example, an electric field can be applied to the site of a cancerous tumor by sweeping through a range of frequencies. Referring now to FIG. 16, exemplary plot 1602 shows an alternating electric field, where the frequency increases over time. Similarly, FIG. 17 shows the change in frequency as a function of time in exemplary plot 1702 during a programmed therapy parameter. In some embodiments, a frequency sweep can include sweeping from a minimum frequency up to a maximum frequency. In some embodiments, a frequency sweep can include sweeping from a maximum frequency down to a minimum frequency. In other embodiments, sweeping from a minimum frequency up to a maximum frequency and sweeping from the maximum frequency down to the minimum frequency can be repeated as many times as desired throughout the duration of the delivery of the electric field from the electric field generating circuit.

As therapy progresses during a frequency sweep, it may be desired to alternate between frequency ranges so that as the cells within a population change in size and number in response to therapy, more cells can be targeted. For example, in some embodiments, a frequency sweep can include alternating between a first frequency sweep covering a range of about 100 kHz to 300 kHz and a second frequency sweep covering a range about 200 kHz to 500 kHz. It will be appreciated that sweeping through a first and second frequency range as described can be performed indefinitely throughout the course of the therapy. In some embodiments, the second frequency sweep (range) can be at higher frequencies than the first frequency sweep (range). In some embodiments, the first frequency sweep (range) can be at higher frequencies than the second frequency sweep (range).

Frequency ranges for the first and second frequency ranges can be any range including specific frequencies recited above with respect to electric field generating circuit 1420, provided that the lower end of each range is a value less than the upper end of each range. At times, it may be beneficial to have some amount of overlap between the frequency range of the first and second frequency sweep.

As described herein, some electrodes of a medical device can be used as sensing electrodes. In some embodiments herein, feedback obtained during electric field therapy can be used to monitor the effectiveness of treating a cancerous tumor with the therapy. Data can be measured for parameters such as impedance, capacitance, field strength, etc. to direct a particular course of treatment. Without being bound by any particular theory, it is believed that a cancerous tumor has a particular impedance associated therewith. The impedance associated with a tumor can change as the size or cellular makeup of the tumor changes. Therefore, impedance can be monitored during the course of an electric field therapy in order to determine if the cancerous tumor is responding to therapy. In some instances, an increase in impedance of the tissue in a treatment area including a cancerous tumor can be indicative of tumor regression. In other instances, a decrease or no observed change in impedance of the tissue in a treatment area can be indicative of tumor progression or lack of change in the tumor respectively. Other physiological properties associated with a cancerous tumor, such as blood flow, metabolite concentrations, systemic cancer markers, and temperature can also be used in conjunction with impedance analysis to monitor the progression or regression of a cancerous tumor in response to electric field therapy.

Therapy parameters including, but not limited to, one or more of the amplitude, frequency, pulse width, waveform, directionality, vector, and/or duty cycle of the electric field therapy can be modulated and/or changed, tuned or otherwise altered based on measured values for at least one of impedance, capacitance, field strength, etc.

Figure 18:
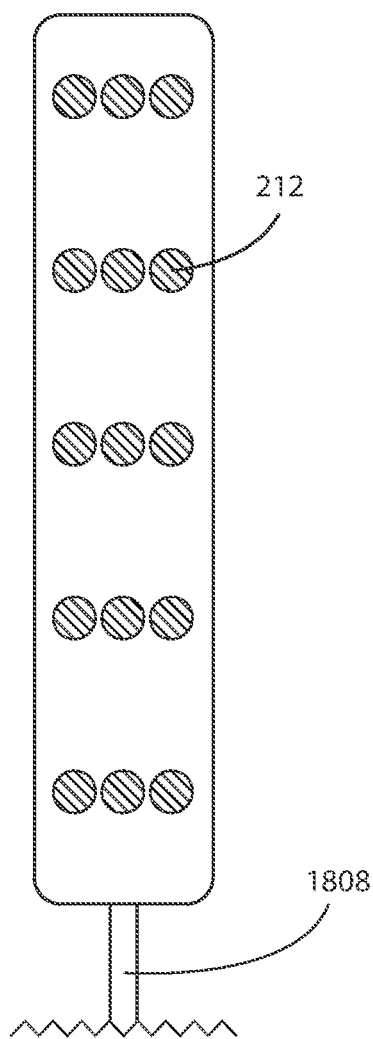
FIG. 18 is a schematic view of a portion of a stimulation lead in accordance with various embodiment herein.

It will be appreciated that electrodes as disposed on electrical stimulation leads can take on many different forms. Referring now to FIG. 18, a schematic view is shown of a portion of a stimulation lead 1808 in accordance with various embodiment herein. In this embodiment, a plurality of electrodes 212 are disposed on the stimulation lead 1808. In this particular example, the electrodes 212 are arrayed in a grid pattern. However, in other embodiments, the electrodes 212 may not be arrayed in a grid pattern. Many different configurations for electrodes are contemplated herein.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

As used herein, the recitation of numerical ranges by endpoints shall include all numbers subsumed within that range (e.g., 2 to 8 includes 2.1, 2.8, 5.3, 7, etc.).

The headings used herein are provided for consistency with suggestions under 37 CFR 1.77 or otherwise to provide organizational cues. These headings shall not be viewed to limit or characterize the invention(s) set out in any claims that may issue from this disclosure. As an example, although the headings refer to a "Field," such claims should not be limited by the language chosen under this heading to describe the so-called technical field. Further, a description of a technology in the "Background" is not an admission that technology is prior art to any invention(s) in this disclosure. Neither is the "Summary" to be considered as a characterization of the invention(s) set forth in issued claims.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

The invention claimed is:

1. A medical device system comprising:
   an electric field generating circuit configured to generate one or more electric fields; and
   control circuitry in communication with the electric field generating circuit, the control circuitry configured to control delivery of the one or more electric fields from the at least one electric field generating circuit;
   one or more electrodes disposed on a first stimulation lead configured to deliver the electric fields to a site of a cancerous tumor within a patient;
   one or more electrodes disposed on a second stimulation lead configured to deliver the electric fields to the site of a cancerous tumor within a patient; and
   one or more surface contact members disposed along the first stimulation lead configured to pivot around the first stimulation lead, the one or more surface contact members comprising a window configured to expose a portion of the one or more electrodes disposed on the first stimulation lead, wherein the window has a width less than a diameter of the first stimulation lead;
   wherein the first and second stimulation leads are configured to be implanted on or about a duodenum;
   wherein the control circuitry causes the electric field generating circuit to generate the one or more electric fields at frequencies selected from a range of between 10 kHz to 1 MHz.

2. The medical device system of claim 1, wherein the first stimulation lead is configured to be affixed to an anterior exterior surface of the duodenum and the second stimulation lead is configured to be affixed to a posterior exterior surface of the duodenum.

3. The medical device system of claim 1, at least one of the first and second stimulation leads comprising one or more thermal shielding pads disposed thereon.

4. The medical device system of claim 3, wherein the thermal shielding pads are configured to pivot around the first or second stimulation lead.

5. The medical device system of claim 1, at least one of the first and second stimulation leads comprising one or more electrical field blocking pads disposed thereon.

6. The medical device system of claim 5, the electrical field blocking pads comprising at least one of a metal grid and a metalized material.

7. The medical device system of claim 1, further comprising a housing, the control circuitry disposed within the housing.

8. The medical device system of claim 1, wherein the electrodes on the first stimulation lead or the electrodes on the second stimulation lead are arranged in a grid.

9. The medical device system of claim 1, comprising four or more electrodes disposed on the first stimulation lead to deliver the electric fields to a site of the cancerous tumor within the patient and four or more electrodes disposed on the second stimulation lead to deliver the electric fields to a site of the cancerous tumor within the patient.

10. The medical device system of claim 1, wherein the one or more surface contact members comprise a surface configured to contact a surface of the duodenum, wherein the surface of the one or more surface contact members comprises a concave shape.

11. The medical device system of claim 1, wherein the one or more surface contact members comprise a surface configured to contact a surface of the duodenum, wherein the surface of the one or more surface contact members comprises an electrical field blocking pad.

12. The medical device system of claim 1, wherein the one or more surface contact members comprises a flexible material.

13. The medical device system of claim 1, wherein the width of the window is configured to expose 5 to 160 degrees of a circumference of the one or more electrodes disposed on the first stimulation lead.

14. A method of treating pancreatic cancer comprising:
positioning a first electrical stimulation lead on or about a posterior exterior surface of a duodenum of a patient, the first electrical stimulation lead comprising a first plurality of electrodes and a first surface contact member disposed thereon, wherein the first surface contact member is configured to pivot around the first electrical stimulation lead, and wherein the first surface contact member comprises a window configured to expose a portion of the first plurality of electrodes, wherein the window is disposed on a side of the surface contact member opposite a side of the surface contact member disposed on the posterior exterior surface of the duodenum;
positioning a second electrical stimulation lead on or about an anterior exterior surface of the duodenum of the patient, the second electrical stimulation lead comprising a second plurality of electrodes and a second surface contact member disposed thereon, wherein the second surface contact member is configured to pivot around the second electrical stimulation lead; and
generating an electrical field between at least one pair of electrodes selected from the first plurality and the second plurality disposed on the electrical stimulation lead, the electric field having frequencies within a range of between 10 kHz to 1 MHz;
wherein the first and/or second surface contact member comprises a surface configured to contact a surface of the duodenum, wherein a surface adjacent to the duodenum of the first and/or second surface contact members comprises an electrical field blocking pad.

15. The method of claim 14, further comprising suturing the first electrical stimulation lead and the second electrical stimulation lead to the duodenum.

16. The method of claim 14, further comprising positioning one or more thermal shielding pads about at least one of the first and second stimulation leads.

17. The method of claim 16, wherein the thermal shielding pads are configured to pivot around the first or second stimulation lead.

18. The method of claim 14, further comprising positioning one or more electrical field blocking pads about at least one of the first and second stimulation leads.

19. The method of claim 18, the electrical field blocking pads comprising at least one of a metal grid and a metalized material.

20. A medical device system comprising:
an electric field generating circuit configured to generate one or more electric fields; and
control circuitry in communication with the electric field generating circuit, the control circuitry configured to control delivery of the one or more electric fields from the at least one electric field generating circuit;
one or more electrodes disposed on a first stimulation lead configured to deliver the electric fields to a site of a cancerous tumor within a patient;
one or more electrodes disposed on a second stimulation lead configured to deliver the electric fields to the site of a cancerous tumor within a patient; and
plurality of surface contact members disposed along the first stimulation lead configured to pivot around the first stimulation lead, the plurality of surface contact members comprising a window configured to expose a portion of the one or more electrodes disposed on the first stimulation lead, wherein the window has a width less than a diameter of the first stimulation lead;
wherein the first and second stimulation leads are configured to be implanted on or about a duodenum;
wherein the control circuitry causes the electric field generating circuit to generate the one or more electric fields at frequencies selected from a range of between 10 kHz to 1 MHz; and
wherein the plurality of surface contact members comprise a surface configured to contact a surface of the duodenum, wherein a surface adjacent to the duodenum of the one or more surface contact members comprises a thermal shielding pad.

* * * * *